US008293965B2

(12) United States Patent
McMaken et al.

(10) Patent No.: US 8,293,965 B2
(45) Date of Patent: Oct. 23, 2012

(54) ANTIMICROBIAL SITE DRESSINGS

(75) Inventors: Jack D. McMaken, West Linn, OR (US); Bruce L. Gibbins, Lake Oswego, OR (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/789,701

(22) Filed: Apr. 25, 2007

(65) Prior Publication Data

US 2007/0293800 A1 Dec. 20, 2007

Related U.S. Application Data

(60) Provisional application No. 60/796,039, filed on Apr. 28, 2006.

(51) Int. Cl.
*A61F 15/00* (2006.01)

(52) U.S. Cl. .............. 602/52; 602/48; 602/42; 604/180; 604/307

(58) Field of Classification Search .................. 604/175, 604/180, 307; 602/43, 48, 47, 42, 46, 50, 602/52, 54; 424/443–449; 128/DIG. 26, 128/DIG. 6
See application file for complete search history.

(56) References Cited

U.S. PATENT DOCUMENTS

| 2,396,515 A | 3/1946 | Kreidl et al. |
| 2,934,066 A | 4/1960 | Stowasser et al. |
| 3,092,552 A | 6/1963 | Romans |
| 3,152,094 A | 10/1964 | Erner et al. |
| 3,152,904 A | 10/1964 | Sorensen et al. |
| 3,157,524 A | 11/1964 | Artandi |
| 3,485,658 A | 12/1969 | Iler |
| 3,511,764 A | 5/1970 | Marans et al. |
| 3,624,835 A | 11/1971 | Wyatt |
| 3,645,835 A | 2/1972 | Hodgson |
| 3,647,439 A | 3/1972 | Bass |
| 3,846,236 A | 11/1974 | Updike et al. |
| 3,933,507 A | 1/1976 | Von Konig et al. |
| 3,969,498 A | 7/1976 | Catania et al. |
| 3,996,141 A | 12/1976 | Updike |
| 4,113,658 A | 9/1978 | Geus |
| 4,130,517 A | 12/1978 | Lundberg et al. |

(Continued)

FOREIGN PATENT DOCUMENTS

AU 2005280443 8/2005

(Continued)

OTHER PUBLICATIONS

Acticoat RTM, Silver Coated Dressing Marketing Materials. The Westaim Corporation, 1988.

(Continued)

*Primary Examiner* — Patricia Bianco
*Assistant Examiner* — Camtu Nguyen
(74) *Attorney, Agent, or Firm* — Dority & Manning, P.A.

(57) ABSTRACT

The present invention comprises antimicrobial articles for use with a percutaneous device, comprising a matrix which may contact the percutaneous device in a three-dimensional mode and release antimicrobial agents (e.g., silver ions) to the percutaneous device access site. In addition, the antimicrobial article of the present invention may donate moisture to a dry dermal site (e.g., a dry wound bed) and/or absorb liquid or exudates of a dermal site. The present invention also comprises methods for treating and/or preventing an infection using the antimicrobial articles of the present invention.

26 Claims, 2 Drawing Sheets

U.S. PATENT DOCUMENTS

| | | | |
|---|---|---|---|
| 4,136,177 A | 1/1979 | Lin et al. | |
| 4,136,178 A | 1/1979 | Lin et al. | |
| 4,260,677 A | 4/1981 | Winslow et al. | |
| 4,306,551 A | 12/1981 | Hymes et al. | |
| 4,310,509 A | 1/1982 | Berglund et al. | |
| 4,320,201 A | 3/1982 | Berg et al. | |
| 4,328,799 A | 5/1982 | LoPiano | |
| 4,340,043 A | 7/1982 | Seymour | |
| 4,364,929 A | 12/1982 | Sasmor et al. | |
| 4,393,048 A | 7/1983 | Mason, Jr. et al. | |
| 4,474,571 A | 10/1984 | Lasley | |
| 4,483,688 A | 11/1984 | Akiyama | |
| 4,529,623 A | 7/1985 | Maggs | |
| 4,604,384 A | 8/1986 | Smith et al. | |
| 4,608,041 A | 8/1986 | Nielsen | |
| 4,612,337 A | 9/1986 | Fox, Jr. et al. | |
| 4,624,656 A | 11/1986 | Clark et al. | |
| 4,686,211 A | 8/1987 | Hara et al. | |
| 4,708,821 A | 11/1987 | Shimokawa et al. | |
| 4,721,724 A | 1/1988 | Stettendorf et al. | |
| 4,747,847 A | 5/1988 | Magruder et al. | |
| 4,782,819 A | 11/1988 | Adair | |
| 4,801,291 A | 1/1989 | Loori | |
| 4,902,503 A | 2/1990 | Umemura et al. | |
| 4,915,694 A * | 4/1990 | Yamamoto et al. | 604/180 |
| 4,969,881 A | 11/1990 | Viesturs | |
| 5,023,082 A | 6/1991 | Friedman et al. | |
| 5,049,139 A | 9/1991 | Gilchrist | |
| 5,076,265 A | 12/1991 | Wokalek | |
| 5,086,620 A | 2/1992 | Spears | |
| 5,091,171 A | 2/1992 | Yu et al. | |
| 5,100,668 A | 3/1992 | Edelman et al. | |
| 5,128,326 A | 7/1992 | Balazs et al. | |
| 5,149,524 A | 9/1992 | Sherba et al. | |
| 5,151,271 A | 9/1992 | Otsuka et al. | |
| 5,158,772 A | 10/1992 | Davis | |
| 5,175,229 A | 12/1992 | Braatz et al. | |
| 5,181,914 A | 1/1993 | Zook | |
| 5,196,190 A | 3/1993 | Nangia et al. | |
| 5,236,421 A * | 8/1993 | Becher | 604/180 |
| 5,270,358 A | 12/1993 | Asmus | |
| 5,326,567 A | 7/1994 | Capelli | |
| 5,342,528 A | 8/1994 | Adachi et al. | |
| 5,354,862 A | 10/1994 | Hsu | |
| 5,407,685 A | 4/1995 | Malchesky et al. | |
| 5,429,591 A | 7/1995 | Yamamoto et al. | |
| 5,432,077 A | 7/1995 | Farrah | |
| 5,447,492 A * | 9/1995 | Cartmell et al. | 602/58 |
| 5,453,401 A | 9/1995 | Grivna et al. | |
| 5,454,886 A | 10/1995 | Burrell et al. | |
| 5,464,610 A | 11/1995 | Hayes, Jr. et al. | |
| 5,470,585 A | 11/1995 | Gilchrist | |
| 5,503,840 A | 4/1996 | Jacobson et al. | |
| 5,508,038 A | 4/1996 | Wang et al. | |
| 5,508,417 A | 4/1996 | Osei-Gyimah et al. | |
| 5,516,502 A | 5/1996 | Dickerson | |
| 5,527,534 A | 6/1996 | Myhling | |
| 5,567,495 A | 10/1996 | Modak et al. | |
| 5,569,207 A * | 10/1996 | Gisselberg et al. | 604/175 |
| 5,593,683 A | 1/1997 | Viegas et al. | |
| 5,599,296 A | 2/1997 | Spears | |
| 5,603,946 A | 2/1997 | Constantine | |
| 5,614,568 A | 3/1997 | Mawatari et al. | |
| 5,660,854 A | 8/1997 | Haynes et al. | |
| 5,681,579 A | 10/1997 | Freeman | |
| 5,683,713 A | 11/1997 | Blank et al. | |
| 5,693,624 A | 12/1997 | Hardy et al. | |
| 5,695,777 A | 12/1997 | Donovan et al. | |
| 5,709,870 A | 1/1998 | Yoshimura et al. | |
| 5,725,491 A | 3/1998 | Tipton et al. | |
| 5,735,251 A | 4/1998 | Hyodo et al. | |
| 5,736,582 A | 4/1998 | Devillez | |
| 5,744,151 A | 4/1998 | Capelli | |
| 5,753,251 A | 5/1998 | Burrell et al. | |
| 5,792,090 A | 8/1998 | Ladin | |
| 5,804,213 A | 9/1998 | Rolf | |
| 5,820,918 A | 10/1998 | Ronan et al. | |
| 5,830,496 A | 11/1998 | Freeman | |
| 5,833,665 A | 11/1998 | Bootman et al. | |
| 5,840,283 A | 11/1998 | Sorenson et al. | |
| 5,853,742 A | 12/1998 | Bartolone et al. | |
| 5,855,570 A | 1/1999 | Scherson et al. | |
| 5,863,548 A | 1/1999 | Elder | |
| 5,863,864 A | 1/1999 | Plath et al. | |
| 5,869,073 A | 2/1999 | Sawan et al. | |
| 5,908,693 A | 6/1999 | Delgado et al. | |
| 5,927,317 A | 7/1999 | Hsia | |
| 5,928,174 A | 7/1999 | Gibbins | |
| 5,951,458 A | 9/1999 | Hastings et al. | |
| 5,961,996 A | 10/1999 | Garson et al. | |
| 5,965,204 A | 10/1999 | Sodervall et al. | |
| 5,972,317 A | 10/1999 | Sorenson et al. | |
| 5,993,790 A | 11/1999 | Strauss | |
| 6,000,403 A | 12/1999 | Cantwell | |
| 6,004,667 A | 12/1999 | Sakurada et al. | |
| 6,011,194 A | 1/2000 | Buglino et al. | |
| 6,014,585 A | 1/2000 | Stoddard | |
| 6,042,845 A | 3/2000 | Sun et al. | |
| 6,051,614 A | 4/2000 | Hirai et al. | |
| 6,099,805 A | 8/2000 | Hartlove | |
| 6,103,868 A | 8/2000 | Heath et al. | |
| 6,110,447 A | 8/2000 | Ramin et al. | |
| 6,113,287 A | 9/2000 | Merz et al. | |
| 6,143,794 A | 11/2000 | Chaudhuri et al. | |
| 6,159,977 A | 12/2000 | Reeves | |
| 6,187,290 B1 | 2/2001 | Gilchrist et al. | |
| 6,191,339 B1 | 2/2001 | Gueret | |
| 6,201,164 B1 | 3/2001 | Wulff et al. | |
| 6,214,360 B1 | 4/2001 | Richter et al. | |
| 6,224,622 B1 | 5/2001 | Kotzev | |
| 6,231,840 B1 | 5/2001 | Buck | |
| 6,235,964 B1 | 5/2001 | Kadash et al. | |
| 6,248,342 B1 | 6/2001 | Trogolo et al. | |
| 6,264,927 B1 | 7/2001 | Monahan | |
| 6,270,811 B1 | 8/2001 | Fregonese | |
| 6,316,084 B1 | 11/2001 | Claus et al. | |
| 6,326,524 B1 | 12/2001 | Fattman et al. | |
| 6,355,858 B1 | 3/2002 | Gibbins | |
| 6,468,989 B1 | 10/2002 | Chang et al. | |
| 6,471,982 B1 | 10/2002 | Lydon et al. | |
| 6,530,895 B1 | 3/2003 | Keirn | |
| 6,605,751 B1 | 8/2003 | Gibbins et al. | |
| 6,669,981 B2 | 12/2003 | Parsons et al. | |
| 6,716,895 B1 | 4/2004 | Terry | |
| 6,897,349 B2 | 5/2005 | Gibbins et al. | |
| 6,921,529 B2 | 7/2005 | Maley | |
| 7,129,389 B1 * | 10/2006 | Watson | 602/48 |
| 7,160,553 B2 | 1/2007 | Gibbins et al. | |
| 7,166,330 B2 | 1/2007 | Takahashi et al. | |
| 7,189,410 B1 | 3/2007 | Drohan et al. | |
| 7,576,255 B2 | 8/2009 | Gibbins et al. | |
| 2001/0026810 A1 | 10/2001 | McGhee et al. | |
| 2001/0041188 A1 | 11/2001 | Gibbins et al. | |
| 2002/0001604 A1 | 1/2002 | Shigeru et al. | |
| 2002/0042587 A1 | 4/2002 | Murdock | |
| 2002/0073891 A1 | 6/2002 | Parsons et al. | |
| 2002/0082340 A1 | 6/2002 | Hanke et al. | |
| 2003/0041188 A1 | 2/2003 | Han et al. | |
| 2003/0083610 A1 | 5/2003 | McGrath et al. | |
| 2003/0093057 A1 | 5/2003 | Zhang et al. | |
| 2003/0186955 A1 | 10/2003 | Vange et al. | |
| 2004/0010215 A1 | 1/2004 | Gibbins et al. | |
| 2004/0062733 A1 | 4/2004 | Birnbaum | |
| 2004/0082925 A1 | 4/2004 | Patel | |
| 2004/0096410 A1 | 5/2004 | Maley et al. | |
| 2004/0108462 A1 | 6/2004 | Besesty et al. | |
| 2004/0127025 A1 | 7/2004 | Crocker et al. | |
| 2004/0147618 A1 | 7/2004 | Lee et al. | |
| 2004/0170545 A1 | 9/2004 | Emanuel | |
| 2004/0173056 A1 | 9/2004 | McNally et al. | |
| 2004/0180093 A1 | 9/2004 | Burton et al. | |
| 2004/0253536 A1 | 12/2004 | Park et al. | |
| 2004/0254532 A1 | 12/2004 | Mehier | |
| 2005/0008861 A1 | 1/2005 | Yadav et al. | |
| 2005/0029121 A1 | 2/2005 | Monzyk et al. | |
| 2005/0186135 A1 | 8/2005 | Howes | |
| 2005/0265894 A1 | 12/2005 | Monzyk et al. | |

| | | | |
|---|---|---|---|
| 2006/0276740 A1 | 12/2006 | Bagley | |
| 2007/0003603 A1 | 1/2007 | Karandikar et al. | |
| 2007/0207335 A1 | 9/2007 | Karandikar et al. | |
| 2007/0254044 A1 | 11/2007 | Karandikar et al. | |
| 2009/0035342 A1 | 2/2009 | Karandikar et al. | |
| 2010/0034882 A1 | 2/2010 | Gibbins et al. | |
| 2010/0190004 A1 | 7/2010 | Gibbins et al. | |

FOREIGN PATENT DOCUMENTS

| | | |
|---|---|---|
| AU | 2007215443 | 2/2007 |
| AU | 2009316270 | 11/2009 |
| AU | 2011202034 | 5/2011 |
| BR | 0513967-8 | 8/2005 |
| BR | 0707602-9 | 2/2007 |
| CA | 2589618 | 8/2005 |
| CA | 2641822 | 2/2007 |
| CA | 2743774 | 11/2009 |
| CN | ZL03820077.5 | 7/2003 |
| CN | 200580028750.9 | 8/2005 |
| CN | 200580028877 | 8/2005 |
| CN | 200780012684.5 | 2/2007 |
| DE | 19631421 A1 | 2/1998 |
| EP | 0072251 A2 | 2/1983 |
| EP | 0297769 A1 | 1/1989 |
| EP | 0489206 A1 | 6/1992 |
| EP | 0500387 | 8/1992 |
| EP | 0707793 A1 | 4/1996 |
| EP | 0709101 A2 | 5/1996 |
| EP | 98961733.7 | 11/1998 |
| EP | 00970522.9 | 9/2000 |
| EP | 00990393.1 | 12/2000 |
| EP | 1245239 A1 | 10/2002 |
| EP | 03772113 | 7/2003 |
| EP | 1388561 A2 | 2/2004 |
| EP | 05778379.7 | 8/2005 |
| EP | 05803114.7 | 8/2005 |
| EP | 05797894.2 | 9/2005 |
| EP | 07750244.1 | 2/2007 |
| EP | 07755996.1 | 4/2007 |
| EP | 09801857.5 | 11/2009 |
| GB | 863875 A | 3/1961 |
| GB | 1471013 A | 4/1977 |
| GB | 1554002 A | 10/1979 |
| GB | 2024012 A | 1/1980 |
| GB | 2134791 A | 8/1984 |
| IN | 397/KOLNP/07 | 8/2005 |
| IN | 735/KOLNP/07 | 8/2005 |
| IN | 3530/KOLNP/2008 | 2/2007 |
| JP | 05-271718 A | 10/1993 |
| JP | 06-145060 A | 5/1994 |
| JP | 6248549 A | 9/1994 |
| JP | 7097767 A | 4/1995 |
| JP | 11302119 A | 11/1999 |
| JP | 2003529630 A | 10/2003 |
| JP | 2004137615 A | 5/2004 |
| JP | 2004161632 A | 6/2004 |
| JP | 2007-523881 | 8/2005 |
| JP | 2008-554343 | 2/2007 |
| MX | MX/a/2007/001203 | 8/2005 |
| MX | MX/a/2008/010225 | 2/2007 |
| MX | MX/a/2011/005436 | 11/2009 |
| NO | 20071000 | 8/2005 |
| NZ | 552928 | 8/2005 |
| NZ | 592438 | 4/2011 |
| WO | WO-84/01721 A1 | 5/1984 |
| WO | WO-88/06894 A1 | 9/1988 |
| WO | WO-90/03810 A1 | 4/1990 |
| WO | WO-96/11572 A1 | 4/1996 |
| WO | WO-98/06260 A1 | 2/1998 |
| WO | WO-98/20719 A1 | 5/1998 |
| WO | PCT/US98/24272 | 11/1998 |
| WO | WO-99/15101 A2 | 4/1999 |
| WO | WO-99/25395 A2 | 5/1999 |
| WO | WO-9926666 A2 | 6/1999 |
| WO | WO-00/09173 A1 | 2/2000 |
| WO | WO-00/15202 A2 | 3/2000 |
| WO | PCT/US00/26890 | 9/2000 |
| WO | PCT/US00/35560 | 12/2000 |
| WO | WO-01/11955 A2 | 2/2001 |
| WO | WO-01/24839 A1 | 4/2001 |
| WO | WO-01/49258 A2 | 7/2001 |
| WO | WO-0226039 A1 | 4/2002 |
| WO | WO-0243743 A1 | 6/2002 |
| WO | WO-02/061403 A1 | 8/2002 |
| WO | WO-02/76518 A1 | 10/2002 |
| WO | WO-03/002089 A1 | 1/2003 |
| WO | PCT/US03/23851 | 7/2003 |
| WO | WO-03/080231 A1 | 10/2003 |
| WO | WO-2004/001880 A1 | 12/2003 |
| WO | WO-2004/010952 A2 | 2/2004 |
| WO | WO-2004/028255 A1 | 4/2004 |
| WO | WO-2004/056404 A2 | 7/2004 |
| WO | PCT/US2005/027260 | 8/2005 |
| WO | PCT/US2005/027261 | 8/2005 |
| WO | PCT/US2005/033600 | 9/2005 |
| WO | WO-2006/015317 A2 | 2/2006 |
| WO | WO-2006/026026 A2 | 3/2006 |
| WO | WO-2006/034249 A2 | 3/2006 |
| WO | PCT/US2007/003390 | 2/2007 |
| WO | PCT/US2007/009997 | 4/2007 |
| WO | WO-2007/095058 A2 | 8/2007 |
| WO | WO-2007/127236 A2 | 11/2007 |
| WO | WO-2008/131070 A1 | 10/2008 |
| WO | PCT/US2009/065764 | 11/2009 |
| WO | PCT/US20009/065764 | 11/2009 |
| ZA | 2007/00825 | 8/2005 |

OTHER PUBLICATIONS

Bharathi, Subramanian et al., "Sol-Gel-Derived Nanocrystalline Gold-Silicate Composite Biosensor," Analytical Communications, 1998, 35: 29-31.

Chase, Grafton D., Pharmaceutical Science by Remington, 14th Edition., Mack Publishing Co., Rheology, Newtonian Flow-Plastic Flow-Pseudoplastic Flow-Dilatant Flow-Methods for Measuring Viscosity-Polymer Solutions-Thixotrophy-Pharmaceutical Applications, 1970, 359-371.

ConvaTec Corp. Aquacel Ag Product Info from website. [internet citation] Retrieved Dec. 9, 2002 from http://www.convatec.com/en_US/company/pr/index.html.

Cooper, Rose, "A Review of the Evidence for the Use of Topical Antimicrobial Agents in Wound Care," World Wide Wounds, 2004, 1-15.

Deitch, E. et al., "Silver-Nylon: a New Antimicrobial Agent". Antimicrobial Agents and Chemotherapy, 1983, 23(3):356-359.

Deitch, E., et al., Abstract, "Silver-impregnated nylon cloth dressing: in vitro and in vivo evaluation of antimicrobial activity," J. Trauma, 1987, pp. 301-304, vol. 27, No. 3.

FDA Approval Letter to begin OxyGenesis marketing. Sep. 19, 2008.

Feng et al, "Study of the initiation mechanism of the vinyl polymerization with the system persulfate/N,N,N',N'-tetramethylethylenediamine," Makromol. Chem. 1988, 189: 77-83.

Fox, Jr., Charles L., "Silver Sulfadiazine—A New Topical", Arch. Surg., vol. 96, pp. 184-188, 1968.

Gibbins et al., AcryDerm Absorbent Oxygen Dressing Point of Use Evaluation: Summary of Results. Draft. Jul. 17, 2009.

Gibbins, B. and Hopman, L., "A Comparison of a New Anti-Microbial Polyacrylate Absorbent Wound Dressing Containing Silver with the Silver-containing Anti-microbial Film Dressings", Presentation at Clinical Symposium on Wound Care, Oct. 2, 2009.

Gibbins, Bruce, "The Antimicrobial Benefits of Silver and the Relevance of Microlattice Technology," Ostomy Wound Manage. Feb. 2003; Suppl:4-7.

Grier, N., "Silver and Its Compounds," Disinfection, Sterilization, and Preservation, 3rd Edition. Seymour S. Block, ed., Lea & Febiger, Philadelphia, 1983; Chapter 18, pp. 375-389.

Hackh's Chemical Dictionary, 4th Edition, McGraw Hill Book Co., New York, 1969; p. 451.

Handbook of Common Polymers, "Polyvinyl Alcohol Including Insolubilised Fibres," Scott & Roff, Jr., W.J., The Chemical Company, 1971, pp. 72-197.

Jia et al., "Effect of locally released oxygen on wound healing," Presented at 18th Annual Meeting of the Wound Healing Society, San Diego, CA. Apr. 2008.

Junhui He et al, "Facile in situ synthesis of noble metal nanoparticles in porous cellulose fibers," Chemistry of Materials, 2003, 15(23): 4401-4406.

Kapoor, Sudhir, "Preparation, Characterization, and Surface Modification of Silver Particles," Langmuir, 1998, 14 (5):1021-1025.

MacKeen, P., et al., "Silver-Coated Nylon Fiber as an Antibacterial Agent," Antimicrobial Agents and Chemotherapy, 1987, 31(1): 93-99.

Milk Composition & Synthesis Resourse Library, Milk Composition-Minerals [retrieved on Dec. 5, 2010], retrieved from the internet:<URL:http://ciasses.ansci.illinois.edu/ansc438/milkcompsynth/milkcomp_minerals.html >.

OxyGenesis Dissolved Oxygen Dressings: Case Review, AcryMed, Inc., Jan. 23, 2010.

Pepe, R.C, Wenninger, J.A., & McEwen, G.N., eds., Int'l Cosmetic Ingredient Dictionary & Handbook, 9th ed., 2002, vol. 2. pp. 177.

Price, William R. et al., "Silver Nitrate Burn Dressing, Treatment of Seventy Burned Persons," American Journal of Surgery, 1966, 112:674-680.

Ratner, Buddy D. et al., ACS Symposium Series, No. 31, The American Chemical Society, Synthetic Hydrogels for Biomedical Applications, pp. 1-36.

Rifai et al., "Facile in Situ Silver Nanoparticle Formation in Insulating Porous Polymer Matrices," Chemistry of Materials 2006; 18(1): 21-25.

Roe, David F., Gibbins, Bruce L., and Ladizinsky, Daniel A., "Topical Dissolved Oxygen Penetrates Skin: Model and Method," J Surg Res. 2010, 159(1):e29-e36.

Russel A. and Hugo, W., "Antimicrobial Activity and Action of Silver," Progress in Medicinal Chemistry, vol. 31, G-.P. Ellis & D.K. Luscombe, ed., Elsevier Science B.V., 1994; pp. 351-370.

Schacht, Etienne H., Hydrogel Drug Delivery Systems, Institute of Organic Chemistry, State University Gent, 1984, pp. 259-278.

Sheehan et al, "Anti-bacterial Silver Coatings on Orthopaedic Metals—An In Vitro and Animal Study," Journal of Bone and Joint Surgery. 2003, 85-B(SUPP_II):141.

Silver, Simon, "Bacterial Silver Resistance: Molecular Biology and Uses and Misuses of Silver Compounds," FEMS Microbiology Reviews, 2003, pp. 341-353.

Topical Delivery Methods, undated reference, retrieved from file on May 11, 2011.

Wang et al., "Directing oleate stabilized nanosized silver colloids into organic phases", Langmuir: The ACS Journal of Surfaces and Colloids. 1998; 14:602-610.

Communication regarding the expiration of opposition period issued on Feb. 10, 2006 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Decision to grant a European Pat. issued on Feb. 24, 2005 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Approval of request for amendments/corrections issued on Feb. 15, 2005 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Reply to communication from the Examining Division filed on Dec. 22, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Result of Consultation by telephone/in person (with time limit) issued on Nov. 9, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Request for correction/amendment of the text proposed for grant filed on Oct. 26, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Communication about intention to grant a European Pat. issued on Jun. 18, 2004 for European Pat. App. No. 98961733.7 which claims priority to PCT/US98/024272 filed on Nov. 13, 1998, published May 27, 1999 as WO 99/027680 (Applicant—Acrymed; Inventors. B.L. Gibbins).

Reply to communication from the Examining Division filed on Aug. 20, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Communication from the Examining Division issued on May 5, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Reply to communication from the Examining Division filed on Feb. 5, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Communication from the Examining Division issued on Aug. 1, 2002 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Reply to communication from the Examining Division filed on May 20, 2002 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Communication from the Examining Division issued Jul. 31, 2001 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

PCT Intl. Search Report issued on Jun. 23, 1999 for PCT/US98/24272, filed on Nov. 13, 1998, published May 27, 1999 as WO 99/027680 (Applicant—Acrymed; Inventors: B.L. Gibbins).

PCT Intl. Preliminary exam report issued on Aug. 8, 2001 for PCT/US98/24272, filed on Nov. 13, 1998, published May 27, 1999 as WO 99/027680 (Applicant—Acrymed; Inventors: B.L. Gibbins).

PCT Written opinion issued on Feb. 18, 2000 for PCT/US98/24272, filed on Nov. 13, 1998, published May 27, 1999 as WO 99/027680 (Applicant—Acrymed; Inventors: B.L. Gibbins).

Issue Notification issued on Jul. 14, 1999 for U.S. Appl. No. 08/971,074, filed Nov. 14, 1997 (Inventor—B.L. Gibbins).

Notice of Allowance issued on Feb. 25, 1999 for U.S. Appl. No. 08/971,074, filed Nov. 14, 1997 (Inventor—B.L. Gibbins).

Examiner Interview Summary/Amendment issued on Dec. 11, 1998 for U.S. Appl. No. 08/971,074, filed Nov. 14, 1997 (Inventor—B.L. Gibbins).

Response after Non-Final Action filed on Nov. 18, 1998 for U.S. Appl. No. 08/971,074, filed Nov. 14, 1997 (Inventor—B.L. Gibbins).

Non-Final Rejection issued on Aug. 19, 1998 for U.S. Appl. No. 08/971,074, filed Nov. 14, 1997 (Inventor—B.L. Gibbins).

Response to Election / Restriction filed on Jul. 10, 1998 for U.S. Appl. No. 08/971,074, filed Nov. 14, 1997 (Inventor—B.L. Gibbins).

Restriction Requirement issued on May 21, 1998 for U.S. Appl. No. 08/971,074, filed Nov. 14, 1997 (Inventor—B.L. Gibbins).

Issue Notification issued on Mar. 12, 2002 for U.S. Appl. No. 09/191,223, filed Nov. 13, 1998 (Inventor—B.L. Gibbins).

Notice of Allowance issued on Sep. 25, 2001 for U.S. Appl. No. 09/191,223, filed Nov. 13, 1998 (Inventor—B.L. Gibbins).

Notice of Allowance issued on Oct. 3, 2000 for U.S. Appl. No. 09/191,223, filed Nov. 13, 1998 (Inventor—B.L. Gibbins).

Response after Non-Final Action filed on Aug. 11, 2000 for U.S. Appl. No. 09/191,223, filed Nov. 13, 1998 (Inventor—B.L. Gibbins).

Non-Final Rejection issued on Apr. 11, 2000 for U.S. Appl. No. 09/191,223, filed Nov. 13, 1998 (Inventor13 B.L. Gibbins).

Response to Election / Restriction filed on Mar. 21, 2000 for U.S. Appl. No. 09/191,223, filed Nov. 13, 1998 (Inventor—B.L. Gibbins).

Restriction Requirement issued on Feb. 22, 2000 for U.S. Appl. No. 09/191,223, filed Nov. 13, 1998 (Inventor—B.L. Gibbins).

Communication regarding the expiry of opposition period issued on Sep. 2, 2009 for EP App. No. 970522.9, which claims priority to Intl.

Pat. App. No. PCT/US00/26890, filed Sep. 29, 200, published on Apr. 12, 2001 as WO 01/024,839 (Applicant—Acrymed, Inc.).
Decision to grant a European Pat. issued on Oct. 2, 2008 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Communication about intention to grant a European Pat. issued on Apr. 10, 2008 for EP App. No. 970522.9, which claims priority to Intl. Pat. App. No. PCT/US00/26890, filed Sep.29, 200, published on Apr. 12, 2001 as WO 01/024839 (Applicant—Acrymed, Inc.).
Reply to communication from the Examining Division filed on Feb. 26, 2008 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Communication from the Examining Division issued on Oct. 18, 2007 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Reply to communication from the Examining Division filed on Dec. 28, 2006 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Communication from the Examining Division issued on Sep. 1, 2006 for EP App. No. 970522.9, which claims priority to Intl. Pat. App. No. PCT/US00/26890, filedSep. 29, 200, published on Apr. 12, 2001 as WO 01/024839 (Applicant—Acrymed, Inc.).
Reply to communication from the Examining Division filed on Mar. 21, 2005 for EP App. No. 970522.9, which claims priority to Intl. Pat. App. No. PCT/US00/26890, filed Sep. 29, 200, published on Apr. 12, 2001 as WO 01/024839 (Applican—Acrymed, Inc.).
Communication from the Examining Division issued on Sep. 20, 2004 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Reply to communication from the Examining Division filed on Feb. 27, 2003 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Communication from the Examining Division issued on Aug. 21, 2002 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
PCT Intl. Search Report issued on Feb. 5, 2001 for PCT/US00/26890, filed on Sep. 29, 2000, published Apr. 12, 2001 as WO 01/24839 (Applicant—Acrymed; Inventors: Gibbins).
PCT Written Opinion issued on Jul. 23, 2001 for PCT/US00/26890, filed on Sep. 29, 2000, published Apr. 12, 2001 as WO 01/24839 (Applicant—Acrymed; Inventors: Gibbins).
PCT Intl. Preliminary Examination Report issued on Oct. 17, 2001 for PCT/US00/26890, filed on Sep. 29, 2000, published Apr. 12, 2001 as WO 01/24839 (Applicant—Acrymed; Inventors: Gibbins).
Notice of Allowance issued on Apr. 15, 2003 for U.S. Appl. No. 09/675,892, filed Sep. 29, 2000 (Inventor—B.L. Gibbins).
Amendment/Response After Non-Final Rejection filed on Mar. 21, 2003 for U.S. Appl. No. 09/675,892, filed Sep. 29, 2000 (Inventor—B.L. Gibbins).
Non-Final Rejection issued on Nov. 21, 2002 for U.S. Appl. No. 09/675,892, filed Sep. 29, 2000 (Inventor—B.L. Gibbins).
Amendment After Final filed on Oct. 30, 2002 for U.S. Appl. No. 09/675,892, filed Sep. 29, 2000 (Inventor—B.L. Gibbins).
Final Rejection issued on Jul. 31, 2002 for U.S. Appl. No. 09/675,892, filed Sep. 29, 2000 (Inventor—B.L. Gibbins).
Amendment/Response After Non-Final Rejection filed on Apr. 18, 2002 for U.S. Appl. No. 09/675,892, filed Sep. 29, 2000 (Inventor—B.L. Gibbins).
Non-Final Rejection issued on Jan. 18, 2002 for U.S. Appl. No. 09/675,892, filed Sep. 29, 2000 (Inventor—B.L. Gibbins).
Notice of Allowance issued on Mar. 7, 2005 for U.S. Appl. No. 10/441,275, filed May 19, 2003 (Inventor—B.L. Gibbins).
Notice of Allowance/Examiner Interview Summary Record issued on Jul. 2, 2004 for U.S. Appl. No. 10/441,275, filed May 19, 2003 (Inventor—B.L. Gibbins).

Examiner Interview Summary Record (PTOL-413) issued May 26, 2004 for U.S. Appl. No. 10/441,275, filed May 19, 2003 (Inventor—B.L. Gibbins).
Supplemental Preliminary Amendment filed on Mar. 25, 2004 for U.S. Appl. No. 10/441,275, filed May 19, 2003 (Inventor—B.L. Gibbins).
Preliminary Amendment filed on Dec. 2, 2003 for U.S. Appl. No. 10/441,275, filed May 19, 2003 (Inventor—B.L. Gibbins).
Issue Notification issued on Jul. 29, 2009 for U.S. Appl. No. 10/978,556, filed Nov. 1, 2004 (Inventor—B.L. Gibbins).
Notice of Allowance issued on Apr. 16, 2009 for U.S. Appl. No. 10/978,556, filed Nov. 1, 2004 (Inventor—B.L. Gibbins).
Terminal Disclaimer/Amendment After Final Rejection filed on Apr. 6, 2009 for U.S. Appl. No. 10/978,556, filed Nov. 1, 2004 (Inventor—B.L. Gibbins).
Final Rejection issued on Nov. 6, 2008 for U.S. Appl. No. 10/978,556, filed Nov. 1, 2004 (Inventor—B.L. Gibbins).
Amendment/Response After Non-Final Rejection filed on Aug. 1, 2008 for U.S. Appl. No. 10/978,556, filed Nov. 1, 2004 (Inventor—B.L. Gibbins).
Non-Final Rejection issued on Apr. 1, 2008 for U.S. Appl. No. 10/978,556, filed Nov. 1, 2004 (Inventor—B.L. Gibbins).
Amendment Submitted/Entered with CPA/RCE filed on Oct. 31, 2007 for U.S. Appl. No. 10/978,556, filed Nov. 1, 2004 (Inventor—B.L. Gibbins).
Advisory Action (PTOL-303) issued on Oct. 3, 2007 for U.S. Appl. No. 10/978,556, filed Nov. 1, 2004 (Inventor—B.L. Gibbins).
Amendment After Final Rejection filed on Sep. 13, 2007 for U.S. Appl. No. 10/978,556, filed Nov. 1, 2004 (Inventor—B.L. Gibbins).
Final Rejection issued on Jul. 13, 2007 for U.S. Appl. No. 10/978,556, filed Nov. 1, 2004 (Inventor—B.L. Gibbins).
Amendment/Response After Non-Final Rejection filed on Apr. 24, 2007 for U.S. Appl. No. 10/978,556, filed Nov. 1, 2004 (Inventor—B.L. Gibbins).
Non-Final Rejection issued on Jan. 24, 2007 for U.S. Appl. No. 10/978,556, filed Nov. 1, 2004 (Inventor—B.L. Gibbins).
Response to Election / Restriction filed on Nov. 13, 2006 for U.S. Appl. No. 10/978,556, filed Nov. 1, 2004 (Inventor—B.L. Gibbins).
Requirement for Restriction/Election issued on Oct. 11, 2006 for U.S. Appl. No. 10/978,556, filed Nov. 1, 2004 (Inventor—B.L. Gibbins).
Preliminary Amendment filed on Feb. 15, 2005 for U.S. Appl. No. 10/978,556, filed Nov. 1, 2004 (Inventor—B.L. Gibbins).
Reexamination Certificate Issued on Jun. 16, 2009 for Inter Partes Reexam No. 95/000,042 of U.S. Pat. 6,605,751 granted Aug. 12, 2003 (Gibbins et al.).
Notice of Intent to Issue a Reexam Certificate issued on Mar. 25, 2009 for Inter Partes Reexam No. 95/000,042 of U.S. Pat. 6,605,751 granted Aug. 12, 2003 (Gibbins et al.).
Right of Appeal Notice issued on Dec. 9, 2008 for Inter Partes Reexam No. 95/000,042 of U.S. Pat. 6,605,751 granted Aug. 12, 2003 (Gibbins et al.).
Action Closing Prosecution (nonfinal) issued on Aug. 19, 2008 for Inter Partes Reexam No. 95/000,042 of U.S. Pat. 6,605,751 granted Aug. 12, 2003 (Gibbins et al.).
Response after non-final action-owner filed on Oct. 8, 2004 for Inter Partes Reexam No. 95/000,042 of U.S. Pat. 6,605,751 granted Aug. 12, 2003 (Gibbins et al.).
Reexam Ordered and Non-Final Action issued on Aug. 4, 2004 for Inter Partes Reexam No. 95/000,042 of U.S. Pat. 6,605,751 granted Aug. 12, 2003 (Gibbins et al.).
Ex Parte Reexam request filed on May 13, 2004 for Inter Partes Reexam No. 95/000,042 of U.S. Pat. 6,605,751 granted Aug. 12, 2003 (Gibbins et al.).
Communication regarding the expiry of opposition period issued on Apr. 4, 2007 for EP App. No. 990393.1, which claims priority to PCT/US00/35560, filed on Dec. 29, 2000, published Jul. 12, 2001 as WO 01/49258 (Applicant—Acrymed).
Decision to grant a European Pat. issued on Apr. 21, 2006 for EP App. No. 990393.1, which claims priority to PCT/US00/35560, filed on Dec. 29, 2000, published Jul. 12, 2001 as WO 01/49258 (Applicant—Acrymed).
Reply to communication about intention to grant filed on Mar. 28, 2006 for EP App. No. 990393.1, which claims priority to PCT/US00/

35560, filed on Dec. 29, 2000, published Jul. 12, 2001 as WO 01/49258 (Applicant—Acrymed).
Communication about intention to grant a European Pat. filed on Nov. 28, 2005 for EP App. No. 990393.1, which claims priority to PCT/US00/35560, filed on Dec. 29, 2000, published Jul. 12, 2001 as WO 01/49258 (Applicant—Acrymed).
Reply to communication from the Examining Division filed on Aug. 30, 2005 for EP App. No. 990393.1, which claims priority to PCT/US00/35560, filed on Dec. 29, 2000, published Jul. 12, 2001 as WO 01/49258 (Applicant—Acrymed).
Communication from the Examining Division issued on Feb. 22, 2005 for EP App. No. 990393.1, which claims priority to PCT/US00/35560, filed on Dec. 29, 2000, published Jul. 12, 2001 as WO 01/49258 (Applicant—Acrymed).
Reply to communication from the Examining Division filed on Apr. 1, 2004 for EP App. No. 990393.1, which claims priority to PCT/US00/35560, filed on Dec. 29, 2000, published Jul. 12, 2001 as WO 01/49258 (Applicant—Acrymed).
Communication from the Examining Division issued on Feb. 13, 2004 for EP App. No. 990393.1, which claims priority to PCT/US00/35560, filed on Dec. 29, 2000, published Jul. 12, 2001 as WO 01/49258 (Applicant—Acrymed).
Reply to communication from the Examining Division filed on Jul. 24, 2003 for EP App. No. 990393.1, which claims priority to PCT/US00/35560, filed on Dec. 29, 2000, published Jul. 12, 2001 as WO 01/49258 (Applicant—Acrymed).
Communication from the Examining Division issued on Jan. 23, 2003 for EP App. No. 990393.1, which claims priority to PCT/US00/35560, filed on Dec. 29, 2000, published Jul. 12, 2001 as WO 01/49258 (Applicant—Acrymed).
Amendments before examination filed on Oct. 18, 2002 for EP App. No. 990393.1, which claims priority to PCT/US00/35560, filed on Dec. 29, 2000, published Jul. 12, 2001 as WO 01/49258 (Applicant—Acrymed).
Amendments before examination filed on Jul. 19, 2002 for EP App. No. 990393.1, which claims priority to PCT/US00/35560, filed on Dec. 29, 2000, published Jul. 12, 2001 as WO 01/49258 (Applicant—Acrymed).
PCT Intl. Search Report issued on Jul. 12, 2001 for PCT/US00/35560, filed on Dec. 29, 2000, published Jul. 12, 2001 as WO 01/49258 (Applicant—Acrymed; Inventors: Gibbins).
PCT Intl. Preliminary Examination Report issued on Apr. 2, 2002 for PCT/US00/35560, filed on Dec. 29, 2000, published Jul. 12, 2001 as WO 01/49258 (Applicant—Acrymed; Inventors: Gibbins).
Non-Final Rejection mailed on Feb. 15, 2011 for U.S. Appl. No. 09/752,939, filed Dec. 29, 2000 (Inventor—Gibbins).
Amendment Submitted/Entered with CPA/RCE filed on Jan. 18, 2011 for U.S. Appl. No. 09/752,939, filed Dec. 29, 2000 (Inventor—Gibbins).
Notice of Appeal filed on Jun. 17, 2010 for U.S. Appl. No. 09/752,939, filed Dec. 29, 2000 (Inventor—Gibbins).
Final Rejection issued on Feb. 25, 2010 for U.S. Appl. No. 09/752,939, filed Dec. 29, 2000 (Inventor—Gibbins).
Amendment/Response After Non-Final Action filed on Dec. 3, 2009 for U.S. Appl. No. 09/752,939, filed Dec. 29, 2000 (Inventor—Gibbins).
Non-Final Rejection issued on Jun. 4, 2009 for U.S. Appl. No. 09/752,939, filed Dec. 29, 2000 (Inventor—Gibbins).
Amendment Submitted/Entered with CPA/RCE filed on Mar. 16, 2009 for U.S. Appl. No. 09/752,939, filed Dec. 29, 2000 (Inventor—Gibbins).
Final Rejection issued on Sep. 18, 2008 for U.S. Appl. No. 09/752,939, filed Dec. 29, 2000 (Inventor—Gibbins).
Amendment/Response After Non-Final Action filed on Apr. 28, 2008 for U.S. Appl. No. 09/752,939, filed Dec. 29, 2000 (Inventor—Gibbins).
Non-Final Rejection issued on Dec. 28, 2007 for U.S. Appl. No. 09/752,939, filed Dec. 29, 2000 (Inventor—Gibbins).
Amendment Submitted/Entered with CPA/RCE filed on Oct. 9, 2007 for U.S. Appl. No. 09/752,939, filed Dec. 29, 2000 (Inventor—Gibbins).
Advisory Action (PTOL-303) issued on Sep. 4, 2007 for U.S. Appl. No. 09/752,939, filed Dec. 29, 2000 (Inventor—Gibbins).
Amendment After Final Rejection filed on Aug. 6, 2007 for U.S. Appl. No. 09/752,939, filed Dec. 29, 2000 (Inventor—Gibbins).
Final Rejection issued on Jun. 6, 2007 for U.S. Appl. No. 09/752,939, filed Dec. 29, 2000 (Inventor—Gibbins).
Supplemental Response/Amendment filed on Apr. 3, 2007 for U.S. Appl. No. 09/752,939 filed Dec. 29, 2000 (Inventor—Gibbins).
Amendment/Response After Non-Final Action filed on Feb. 14, 2007 for U.S. Appl. No. 09/752,939, filed Dec. 29, 2000 (Inventor—Gibbins).
Examiner Interview Summary Record (PTOL-413) issued on Jan. 17, 2007 for U.S. Appl. No. 09/752,939, filed Dec. 29, 2000 (Inventor—Gibbins).
Non-Final Rejection issued on Sep. 14, 2006 for U.S. Appl. No. 09/752,939, filed Dec. 29, 2000 (Inventor—Gibbins).
Amendment Submitted/Entered with CPA/RCE filed on Aug. 7, 2006 for U.S. Appl. No. 09/752,939, filed Dec. 29, 2000 (Inventor—Gibbins).
Amendment initialed by Examiner/Advisory Action (PTOL-303) issued on May 18, 2006 for U.S. Appl. No. 09/752,939, filed Dec. 29, 2000 (Inventor—Gibbins).
Amendment After Final Rejection filed on May 8, 2006 for U.S. Appl. No. 09/752,939, filed Dec. 29, 2000 (Inventor—Gibbins).
Final Rejection issued on Mar. 7, 2006 for U.S. Appl. No. 09/752,939, filed Dec. 29, 2000 (Inventor—Gibbins).
Amendment/Response After Non-Final Action filed on Dec. 1, 2005 for U.S. Appl. No. 09/752,939, filed Dec. 29, 2000 (Inventor—Gibbins).
Non-Final Rejection issued on Aug. 2, 2005 for U.S. Appl. No. 09/752,939, filed Dec. 29, 2000 (Inventor—Gibbins).
Amendment Submitted/Entered with CPA/RCE filed on Jun. 15, 2005 for U.S. Appl. No. 09/752,939, filed Dec. 29, 2000 (Inventor—Gibbins).
Advisory Action (PTOL-303) issued on Jun. 8, 2005 for U.S. Appl. No. 09/752,939, filed Dec. 29, 2000 (Inventor—Gibbins).
Amendment After Final Rejection filed on Mar. 30, 2005 for U.S. Appl. No. 09/752,939, filed Dec. 29, 2000 (Inventor—Gibbins).
Final Rejection issued on Dec. 16, 2004 for U.S. Appl. No. 09/752,939, filed Dec. 29, 2000 (Inventor—Gibbins).
Amendment/Response After Non-Final Action filed on Sep. 16, 2004 for U.S. Appl. No. 09/752,939, filed Dec. 29, 2000 (Inventor—Gibbins).
Non-Final Rejection issued on May 17, 2004 for U.S. Appl. No. 09/752,939, filed Dec. 29, 2000 (Inventor—Gibbins).
Decision to Withdraw from Issue issued on Apr. 26, 2004 for U.S. Appl. No. 09/752,939, filed Dec. 29, 2000 (Inventor—Gibbins).
Notice of Allowance issued on Jan. 23, 2003 for U.S. Appl. No. 09/752,939, filed Dec. 29, 2000 (Inventor—Gibbins).
Amendment Submitted/Entered with CPA/RCE filed on Nov. 15, 2002 for U.S. Appl. No. 09/752,939, filed Dec. 29, 2000 (Inventor—Gibbins).
Advisory Action (PTOL-303) issued on Nov. 19, 2002 for U.S. Appl. No. 09/752,939, filed Dec. 29, 2000 (Inventor—Gibbins).
Amendment After Final Rejection filed on Oct. 15, 2002 for U.S. Appl. No. 09/752,939, filed Dec. 29, 2000 (Inventor—Gibbins).
Final Rejection issued on Jul. 15, 2002 for U.S. Appl. No. 09/752,939, filed Dec. 29, 2000 (Inventor—Gibbins).
Amendment/Response After Non-Final Action filed on Apr. 18, 2002 for U.S. Appl. No. 09/752,939, filed Dec. 29, 2000 (Inventor—Gibbins).
Examiner Interview Summary Record (PTOL-413) issued on Apr. 11, 2002 for U.S. Appl. No. 09/752,939, filed Dec. 29, 2000 (Inventor—Gibbins).
Non-Final Rejection issued on Dec. 18, 2001 for for U.S. Appl. No. 09/752,939, filed Dec. 29, 2000 (Inventor—Gibbins).
Issue Notification issued on Dec. 20, 2006 for U.S. Appl. No. 10/441,141, filed May 19, 2003 (Inventor—Gibbins).
Notice of Allowance/Examiner Interview Summary Record (PTOL-413) issued on Jul. 25, 2006 for U.S. Appl. No. 10/441,141, filed May 19, 2003 (Inventor—Gibbins).
Amendment After Final Rejection filed on Jul. 5, 2006 for U.S. Appl. No. 10/441,141, filed May 19, 2003 (Inventor—Gibbins).

Examiner Interview Summary Record (PTOL-413) issued on Jun. 28, 2006 for U.S. Appl. No. 10/441,141, filed May 19, 2003 (Inventor—Gibbins).

Final Rejection issued on May 4, 2006 for U.S. Appl. No. 10/441,141, filed May 19, 2003 (Inventor—Gibbins).

Amendment/Response After Non-Final Action filed on Feb. 14, 2006 for U.S. Appl. No. 10/441,141, filed May 19, 2003 (Inventor—Gibbins).

Non-Final Rejection issued on Nov. 15, 2005 for U.S. Appl. No. 10/441,141, filed May 19, 2003 (Inventor—Gibbins).

Preliminary Amendment filed on Apr. 12, 2003 for U.S. Appl. No. 10/441,141, filed May 19, 2003 (Inventor—Gibbins).

Notification of Grant issued Feb. 5, 2010 for Chinese Pat. App. No. 03820077.5, which claims priority to PCT/US03/023851 filed Jul. 29, 2003, published Feb. 5, 2004 as WO 04/010952 (Applicant—Acrymed, Inc.).

Response to fifth Office Action filed on Jan. 7, 2010 for Chinese Pat. App. No. 03820077.5, which claims priority to PCT/US03/023851 filed Jul. 29, 2003, published Feb. 5, 2004 as WO 04/010952 (Applicant—Acrymed, Inc.) + claims in English.

Fifth Office Action issued on Oct. 23, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.).

Response to fourth Office Action filed on Sep. 11, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.)—English translation only.

Fourth Office Action issued on Apr. 17, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.).

Response to third Office Action filed on Aug. 27, 2008 for Chinese Pat. App. No. 03820077.5, which claims priority to PCT/US03/023851 filed Jul. 29, 2003, published Feb. 5, 2004 as WO 04/010952 (Applicant—Acrymed, Inc.) claims in English.

Third Office Action issued on Jun. 13, 2008 for Chinese Pat. App. No. 03820077.5, which claims priority to PCT/US03/023851 filed Jul. 29, 2003, published Feb. 5, 2004 as WO 04/010952 (Applicant—Acrymed, Inc.).

Response to Second Office Action filed on Dec. 25, 2007 for Chinese Pat. App. No. 03820077.5, which claims priority to PCT/US03/023851 filed Jul. 29, 2003, published Feb. 5, 2004 as WO 04/010952 (Applicant—Acrymed, Inc.)—no translation available.

Second Office Action issed for Aug. 10, 2007 for Chinese Pat. App. No. 03820077.5, which claims priority to PCT/US03/023851 filed Jul. 29, 2003, published Feb. 5, 2004 as WO 04/010952 (Applicant—Acrymed, Inc.).

Response to first Office Action filed on Sep. 1, 2006 for Chinese Pat. App. No. 03820077.5, which claims priority to PCT/US03/023851 filed Jul. 29, 2003, published Feb. 5, 2004 as WO 04/010952 (Applicant—Acrymed, Inc.)—no translation available.

First Office Action issued on Apr. 21, 2006 for Chinese Pat. App. No. 03820077.5, which claims priority to PCT/US03/023851 filed Jul. 29, 2003, published Feb. 5, 2004 as WO 04/010952 (Applicant—Acrymed, Inc.).

Decision to Grant pursuant to Article 97(2) EPC issued on Dec. 2, 2010 for EP App. No. 3772113.1, which claims priority to PCT/US03/023851 filed Jul. 29, 2003, published Feb. 5, 2004 as WO 04/010952 (Applicant—Acrymed, Inc.).

Communication under Rule 71(3) EPC issued on Jun. 4, 2010 for EP App. No. 3772113.1, which claims priority to PCT/US03/023851 filed Jul. 29, 2003, published Feb. 5, 2004 as WO 04/010952 (Applicant—Acrymed, Inc.).

Letter during examination procedure after communication from the Examining Division filed on Jan. 19, 2010 for EP App. No. 3772113.1, which claims priority to PCT/US03/023851 filed Jul. 29, 2003, published Feb. 5, 2004 as WO 04/010952 (Applicant—Acrymed, Inc.).

Reply to communication from the Examining Division filed on Jan. 13, 2010 for EP App. No. 3772113.1, which claims priority to PCT/US03/023851 filed Jul. 29, 2003, published Feb. 5, 2004 as WO 04/010952 (Applicant—Acrymed, Inc.).

Communication from the Examining Division issued on Jul. 3, 2009 for EP App. No. 3772113.1, which claims priority to PCT/US03/023851 filed Jul. 29, 2003, published Feb. 5, 2004 as WO 04/010952 (Applicant—Acrymed, Inc.).

Reply to communication from the Examining Division filed on Jul. 15, 2008 for EP App. No. 3772113.1, which claims priority to PCT/US03/023851 filed Jul. 29, 2003, published Feb. 5, 2004 as WO 04/010952 (Applicant—Acrymed, Inc.).

Communication from the Examining Division issued on Jan. 10, 2008 for EP App. No. 3772113.1, which claims priority to PCT/US03/023851 filed Jul. 29, 2003, published Feb. 5, 2004 as WO 04/010952 (Applicant—Acrymed, Inc.).

Supplementary European search report issued on Dec. 14, 2006 for EP App. No. 3772113.1, which claims priority to PCT/US03/023851 filed Jul. 29, 2003, published Feb. 5, 2004 as WO 04/010952 (Applicant—Acrymed, Inc.).

Preliminary Amendment filed on Apr. 12, 2005 for EP App. No. 3772113.1, which claims priority to PCT/US03/023851 filed Jul. 29, 2003, published Feb. 5, 2004 as WO 04/010952 (Applicant—Acrymed, Inc.).

PCT Intl. Search Report issued on Aug. 27, 2004 for Intl. App. No. PCT/US03/023851 filed Jul. 29, 2003, published Feb. 5, 2004 as WO 04/010952 (Applicant—AcryMed, Inc.).

Issue Notification issued on Jul. 6, 2005 for U.S. Appl. No. 10/207,936, filed Jul. 29, 2002 (Inventor—Maley, J. C.).

Amendment/Response—After Non-Final Rejection filed on Apr. 25, 2005 for U.S. Appl. No. 10/207,936, filed Jul. 29, 2002 (Inventor—Maley, J. C.).

Office Communication issued on Mar. 30, 2005 for U.S. Appl. No. 10/207,936, filed Jul. 29, 2002 (Inventor—Maley, J. C.).

Notice of Allowance and Fees Due (PTOL-85) with Examiner Interview Summary Record (PTOL-413) issued Feb. 16, 2005 for U.S. Appl. No. 10/207,936, filed Jul. 29, 2002 (Inventor—Maley, J. C.).

Supplemental Amendment after Final Rejection issed on Jan. 28, 2005 for U.S. Appl. No. 10/207,936, filed Jul. 29, 2002 (Inventor—Maley, J. C.).

Amendment After Final Rejection filed on Jan. 12, 2005 for U.S. Appl. No. 10/207,936, filed Jul. 29, 2002 (Inventor—Maley, J. C.).

Final Rejection issued on Nov. 23, 2004 for U.S. Appl. No. 10/207,936, filed Jul. 29, 2002 (Inventor—Maley, J. C.).

Response After Non-Final Rejection filed on Jul. 29, 2004 for U.S. Appl. No. 10/207,936, filed Jul. 29, 2002 (Inventor—Maley, J. C.).

Non-Final Rejection issued on Apr. 29, 2004 for U.S. Appl. No. 10/207,936, filed Jul. 29, 2002 (Inventor—Maley, J. C.).

Response After Non-Final Rejection filed on Jan. 22, 2004 for U.S. Appl. No. 10/207,936, filed Jul. 29, 2002 (Inventor—Maley, J. C.).

Non-Final Rejection issued on Oct. 22, 2003 for U.S. Appl. No. 10/207,936, filed Jul. 29, 2002 (Inventor—Maley, J. C.).

Response After Non-Compliant Amendment filed on Jun. 2, 2010 for U.S. Appl. No. 10/630,627, filed Jul. 29, 2003 (Inventor—Maley, J.C.).

Amendment Submitted/Entered with CPA/RCE filed on Apr. 27, 2010 for U.S. Appl. No. 10/630,627, filed Jul. 29, 2003 (Inventor—Maley, J.C.).

Final Rejection issued on Dec. 3, 2009 for U.S. Appl. No. 10/630,627, filed Jul. 29, 2003 (Inventor—Maley, J.C.).

Response After Non-Final Rejection filed on Jul. 20, 2009 for U.S. Appl. No. 10/630,627, filed Jul. 29, 2003 (Inventor—Maley, J.C.).

Non-Final Rejection issued on Feb. 19, 2009 for U.S. Appl. No. 10/630,627, filed Jul. 29, 2003 (Inventor—Maley, J.C.).

Amendment Submitted/Entered with CPA/RCE filed on Nov. 26, 2008 for U.S. Appl. No. 10/630,627, filed Jul. 29, 2003 (Inventor—Maley, J.C.).

Final Rejection issued on Jun. 26, 2008 for U.S. Appl. No. 10/630,627, filed Jul. 29, 2003 (Inventor—Maley, J.C.).

Response After Non-Final Rejection filed on Feb. 7, 2008 for U.S. Appl. No. 10/630,627, filed Jul. 29, 2003 (Inventor—Maley, J.C.).

Non-Final Rejection issued on Sep. 7, 2007 for U.S. Appl. No. 10/630,627, filed Jul. 29, 2003 (Inventor—Maley, J.C.).

Amendment Submitted/Entered with CPA/RCE filed on Jun. 22, 2007 for U.S. Appl. No. 10/630,627, filed Jul. 29, 2003 (Inventor—Maley, J.C.).

Advisory Action (PTOL-303) issued on May 17, 2007 for U.S. Appl. No. 10/630,627, filed Jul. 29, 2003 (Inventor—Maley, J.C.).
Amendment After Final Rejection filed on Apr. 23, 2007 for U.S. Appl. No. 10/630,627, filed Jul. 29, 2003 (Inventor—Maley, J.C.).
Final Rejection issued on Feb. 23, 2007 for U.S. Appl. No. 10/630,627, filed Jul. 29, 2003 (Inventor—Maley, J.C.).
Response After Non-Final Rejection filed on Nov. 21, 2006 for U.S. Appl. No. 10/630,627, filed Jul. 29, 2003 (Inventor—Maley, J.C.).
Non-Final Rejection issued on Aug. 24, 2006 for U.S. Appl. No. 10/630,627, filed Jul. 29, 2003 (Inventor—Maley, J.C.).
Response to Election / Restriction Filed on Jun. 23, 2006 for U.S. Appl. No. 10/630,627, filed Jul. 29, 2003 (Inventor—Maley, J.C.).
Restriction/Election Requirement issued on May 23, 2006 for U.S. Appl. No. 10/630,627, filed Jul. 29, 2003 (Inventor—Maley, J.C.).
Second Office Action issued on Aug. 12, 2011 for Chinese Pat. App. No. 200580028750.9, which claims priority to Intl. App. No. PCT/US/05/027260 filed Aug. 1, 2005, published Feb. 9, 2006 as WO 06/015317 (Applicant—Acrymed, Inc.).
Response to First Office Action filed on Jul. 9, 2009 for Chinese Pat. App. No. 200580028750.9, which claims priority to Intl. App. No. PCT/US/05/027260 filed Aug. 1, 2005, published Feb. 9, 2006 as WO 06/015317 (Applicant—Acrymed, Inc.)—Proposed Claims in English.
First Office Action issued on Dec. 26, 2008 for Chinese Pat. App. No. 200580028750.9, which claims priority to Intl. App. No. PCT/US/05/027260 filed Aug. 1, 2005, published Feb. 9, 2006 as WO 06/015317 (Applicant—Acrymed, Inc.).
Amended claims filed on Feb. 26, 2007 for EP App. No. 05778379.7, which claims priority to Intl. App. No. PCT/US05/027260 filed Aug. 1, 2005, published Feb. 9, 2006 as WO 06/015317 (Applicant—Acrymed, Inc.).
Response to Examiner's Report filed on Jun. 29, 2011 for Indian Pat. App 735/KOLNP/2007, which claims priority to Intl. Pat. App. No. PCT/US05/027260, filed on Aug. 1, 2005, published on Mar. 9, 2006 as WO 06/015317 (Applicant—Acrymed, Inc.).
Examiner's Report issued on Jun. 29, 2010 for Indian Pat. App 735/KOLNP/2007, which claims priority to Intl. Pat. App. No. PCT/US05/027260, filed on Aug. 1, 2005, published on Mar. 9, 2006 as WO 06/015317 (Applicant—Acrymed, Inc.).
Intl. Preliminary Report on Patentability issued on Jan. 30, 2007 for Intl. App. No. PCT/US05/027260 filed Aug. 1, 2005, published Feb. 9, 2006 as WO 06/015317 (Applicant—Acrymed, Inc.).
Intl. Search Report with Written Opinion issued on Apr. 28, 2006 for Intl. App. No. PCT/US05/027260 filed Aug. 1, 2005, published Feb. 9, 2006 as WO 06/015317 (Applicant—Acrymed, Inc.).
Protest Documents from 3rd Party filed on Apr. 3, 2009 for U.S. Appl. No. 11/572,899, filed May 13, 2008 (Inventor—Karandikar et al.).
Preliminary Amendment filed on Jan. 29, 2007 for U.S. Appl. No. 11/572,899, filed May 13, 2008 (Inventor—Karandikar et al.).
Intl. Preliminary Report on Patentability issued on Jan. 30, 2007 for Intl. App. No. PCT/US05/027261 filed Aug. 1, 2005, published Mar. 9, 2006 as WO 06/026026 (Applicant—Acrymed, Inc.).
Intl. Search Report with Written Opinion issued on Apr. 28, 2006 for Intl. App. No. PCT/US05/027261 filed Aug. 1, 2005, published Mar. 9, 2006 as WO 06/026026 (Applicant—Acrymed, Inc.).
Notice of Acceptance issued on Jan. 24, 2011 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Response to Examiner's Report filed on Dec. 13, 2010 for AU Pat. App. No. 2005280443, which claims priority to Intl. Pat. App. No. PCT/US05/027261, filed on Aug. 1, 2005, published on 3-92006 as WO 06/02026 (Applicant—Acrymed, Inc.).
Examiner's First Report issued on Feb. 19, 2010 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
AU Divisional App. No. 2011202034 filed on May 3, 2011 from AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Second Office Action (Text Portion) issued on Jun. 7, 2011 for Chinese Pat. App. No. 200580028877.0, which claims priority to Intl.

Pat. App. No. PCT/US05/027261, filed on Aug. 1, 2005, published on Mar. 9, 2006 as WO 06/02026 (Applicant—Acrymed, Inc.).
Response to Office Action filed on Jul. 9, 2009 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
First Office Action issued on Dec. 26, 2008 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
Response to Examiner's Report filed on Jun. 30, 2011 for Indian Pat. App 397/KOLNP/2007, which claims priority to Intl. Pat. App. No. PCT/US05/027261, filed on Aug. 1, 2005, published on Mar. 9, 2006 as WO 06/02026 (Applicant—Acrymed, Inc.)—proposed amendments only.
Examiner's Report issued on Jul. 2, 2010 for Indian Pat. App 397/KOLNP/2007, which claims priority to Intl. Pat. App. No. PCT/US05/027261, filed on Aug. 1, 2005, published on Mar. 9, 2006 as WO 06/02026 (Applicant—Acrymed, Inc.).
Official Action issued on Mar. 1, 2011 for JP App. No. 2007-523881, which claims priority to Intl. Pat. App. No. PCT/US05/027261, filed on Aug. 1, 2005, published on Mar. 9, 2006 as WO 06/02026 (Applicant—Acrymed, Inc.)—translation included.
Notice of Acceptance issued on Apr. 26, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response to Examination Report filed on Apr. 21, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examination Report issued on Feb. 2, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response to Examination Report filed on Jan. 20, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Further Examination Report issued on Jul. 8, 2010 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response and Amended Pages filed on Jun. 28, 2010 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examination Report issued on Apr. 24, 2009 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
NZ Divisional App. No. 592438 filed on Apr. 21, 2011 from New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examiner's first report issued on Oct. 18, 2010 for Australian Pat. App. No. 2007215443, which claims priority to PCT/US07/03390, filed Feb. 8, 2007, published on Aug. 23, 2007 as WO 07/095058 (Applicant—Acrymed, Inc.).
Response to Second Office Action filed on Jun. 7, 2011 for Chinese Pat. App. No. 200780012684.5, which claims priority to PCT/US07/003390 filed on Feb. 8,2007 (Applicant—AcryMed, Inc.)—No Translation.
Second Office Action issued Mar. 23, 2011 for Chinese Pat. App. No. 200780012684.5, which claims priority to PCT/US07/003390 filed on Feb. 8,2007 (Applicant—AcryMed, Inc.).
Response to First Office Action filed on Feb. 28, 2011 for Chinese Pat. App. No. 200780012684.5, which claims priority to PCT/US07/003390 filed on Feb. 8,2007 (Applicant—AcryMed, Inc.)—Proposed amended claims in English.
First Office Action issued Oct. 13, 2010 for Chinese Pat. App. No. 200780012684.5, which claims priority to PCT/US07/003390 filed on Feb. 8,2007 (Applicant—AcryMed, Inc.).

Claim amendments filed on Sep. 4, 2008 for EP App. No. 07750244.1, which claims priority to PCT/US07/03390, filed Feb. 8, 2007, published on Aug. 23, 2007 as WO 07/095058 (Applicant—Acrymed, Inc.).
PCT Preliminary Report on Patentability issued on Aug. 12, 2008 for Intl. Pat. App. No. PCT/US07/03390, filed Feb. 8, 2007, published on Aug. 23, 2007 as WO 07/095058 (Applicant—Acrymed, Inc.).
PCT Intl. Search Report with Written Opinion issued on Dec. 21, 2007 for Intl. Pat. App. No. PCT/US07/03390, filed Feb. 8, 2007, published on Aug. 23, 2007 as WO 07/095058 (Applicant—Acrymed, Inc.).
Amendment Entered with CPA/RCE filed on Apr. 22, 2011 for U.S. Appl. No. 11/704,167, filed Feb. 8, 2007 (Inventors—Karandikar et al.).
Final Rejection issued on Dec. 22, 2010 for U.S. Appl. No. 11/704,167, filed Feb. 8, 2007 (Inventors—Karandikar et al.).
Response after Non-Final Action mailed Oct. 28, 2010 for U.S. Appl. No. 11/704,167, filed Aug. 2, 2007 (Inventors—Karandikar et al.).
Non-Final Rejection issued on May 28, 2010 for U.S. Appl. No. 11/704,167, filed Feb. 8, 2007 (Inventors—Karandikar et al.).
Response to Election / Restriction filed on Apr. 30, 2010 for U.S. Appl. No. 11/704,167, filed Aug. 2, 2007 (Inventors—Karandikar et al.).
Restriction/Election Requirement issued on Mar. 30, 2010 for U.S. Appl. No. 11/704,167, filed Feb. 8, 2007 (Inventors—Karandikar et al.).
Preliminary Amendments filed on Nov. 24, 2008 for EP 07755996.1 which claims priority to PCT/US07/009997, filed on Apr. 25, 2007, published on Nov. 8, 2007 as WO 07/127236 (Applicant—Acrymed, Inc.).
Intl. Search Report w/ Written Opinion issued on Aug. 25, 2008 for Intl. Pat. App. No. PCT/US07/009997, filed on Apr. 25, 2007, published on Nov. 8, 2007 as WO 07/127236 (Applicant—Acrymed, Inc.).
Intl. Preliminary Report on Patentability issued on Oct. 28, 2008 for Intl. Pat. App. No. PCT/US07/009997, filed on Apr. 25, 2007, published on Nov. 8, 2007 as WO 07/127236 (Applicant—Acrymed, Inc.).
Intl. Preliminary Report on Patentability issued on May 24, 2011 for Intl. Pat. App. No. PCT/US09/065764, filed on Nov. 24, 2009, published on May 27, 2010 as WO 10/060094 (Applicant—Kimberly-Clark, Worldwide Inc..).
Intl. Search Report with Written Opinion issued on Apr. 28, 2010 for Intl. Pat. App. No. PCT/US09/065764, filed on Nov. 24, 2009, published on May 27, 2010 as WO 10/060094 (Applicant—Kimberly-Clark, Worldwide Inc.).
Reply to Communication from Examining Division filed on Jun. 16, 2011 for EP App. No. 05797894.2, which claims priority to PCT/US05/033600, filed Sep. 19, 2005, published on Mar. 30, 2006 as WO 06/034249 (Applicant—Acrymed, Inc.).
Communication from Examining Division issued on Feb. 8, 2011 for EP App. No. 05797894.2, which claims priority to PCT/US05/033600, filed Sep. 19, 2005, published on Mar. 30, 2006 as WO 06/034249 (Applicant—Acrymed, Inc.).
Reply to Communication from Examining Division filed on Jun. 23, 2009 for EP App. No. 05797894.2, which claims priority to PCT/US05/033600, filed Sep. 19, 2005, published on Mar. 30, 2006 as WO 06/034249 (Applicant—Acrymed, Inc.).
Communication from Examining Division issued on Dec. 17, 2008 for EP App. No. 05797894.2, which claims priority to PCT/US05/033600, filed Sep. 19, 2005, published on Mar. 30, 2006 as WO 06/034249 (Applicant—Acrymed, Inc.).
Supplemental European Search Report and Opinion issued on Oct. 21, 2008 for EP App. No. 05797894.2, which claims priority to PCT/US05/033600, filed Sep. 19, 2005, published on Mar. 30, 2006 as WO 06/034249 (Applicant—Acrymed, Inc.).
Amendments before examination filed on Apr. 18, 2007 for EP App. No. 05797894.2, which claims priority to PCT/US05/033600, filed Sep. 19, 2005, published on Mar. 30, 2006 as WO 06/034249 (Applicant—Acrymed, Inc.).
Intl. Preliminary Report on Patentability issued on May 1, 2007 for Intl. Pat. App. No. PCT/US05/033600, filed Sep. 19, 2005, published Mar. 30, 2006 as WO 06/034249 (Applicant—Acrymed, Inc.).
Intl. Search Report with Written Opinion issued on Apr. 18, 2007 for Intl. Pat. App. No. PCT/US05/033600, filed on Sep. 19, 2005, published on Mar. 30, 2006 as WO 06/034249 (Applicant—Acrymed, Inc.).
Final Rejection issued on Jun. 13, 2011 for U.S. Appl. No. 11/663,236, filed Mar. 19, 2007 (Karandikar et al.).
Response after Non-Final Action filed on Apr. 12, 2011 for U.S. Appl. No. 11/663,236, filed Mar. 19, 2007 (Karandikar et al.).
Non-Final Rejection issued on Dec. 13, 2010 for U.S. Appl. No. 11/663,236, filed Mar. 19, 2007 (Karandikar et al.).
Response to Restriction/Election Requirement filed on Sep. 23, 2010 for U.S. Appl. No. 11/663,236, filed Mar. 19, 2007 (Karandikar et al.).
Restriction/Election Requirement issued on Jun. 23, 2010 for U.S. Appl. No. 11/663,236, filed Mar. 19, 2007 (Karandikar et al.).
Preliminary Amendment filed on Mar. 19, 2007 for U.S. Appl. No. 11/663,236, filed Mar. 19, 2007 (Karandikar et al.).
Third Office Action issued Jul. 7, 2011 for Chinese Pat. App. No. 200780012684.5, which claims priority to PCT/US07/003390 filed on Feb. 8,2007 (Applicant—AcryMed, Inc.).
Non-Final Rejection issued on Jun. 28, 2011 for U.S. Appl. No. 10/630,627, filed Jul. 29, 2003 (Inventor—Maley, J.C.).
Notice of Allowance issued on May 12, 2011 for U.S. Appl. No. 12/510,651, filed on Jul. 28, 2009 (Inventor—Gibbins).
Amendment/Response After Non-Final Reject/Terminal Disclaimer filed on Apr. 4, 2011 for U.S. Appl. No. 12/510,651, filed Jul. 28, 2009 (Inventor—Gibbins).
Non-Final Rejection issued on Jan. 5, 2011 for U.S. Appl. No. 12/510,651, filed Jul. 28, 2009 (Inventor—Gibbins).
Preliminary Amendment filed on Oct. 28, 2009 for U.S. Appl. No. 12/510,651, filed Jul. 28, 2009 (Inventor—Gibbins).
Response to Restriction Requirement filed on Aug. 9, 2011 for U.S. Appl. No. 11/572,899, filed May 13, 2008 (Inventor—Karandikar et al.).
Restriction requirement issued on Jun. 28, 2011 for U.S. Appl. No. 11/572,899, filed May 13, 2008 (Inventor—Karandikar et al.).
Supplemental European Search Report issued May 23, 2011 for EP App. No. 07750244.1, which claims priority to PCT/US07/03390, filed Feb. 8, 2007, published on Aug. 23, 2007 as WO 07/095058 (Applicant—Acrymed, Inc.).
Non-Final Rejection issued on Jun. 30, 2011 for U.S. Appl. No. 11/704,167, filed Feb. 8, 2007 (Inventors—Karandikar et al.).
Amendment/Response After Non-Final Action filed on Aug. 9, 2011 for U.S. Appl. No. 09/752,939, filed Dec. 29, 2000 (Inventor—Gibbins).
Non-Final Rejection issued on Aug. 17, 2011 for U.S. Appl. No. 12/510,651, filed Jul. 28, 2009 (Inventor—Gibbins).
Response after Non-Final Rejection filed on Aug. 26, 2011 for U.S. Appl. No. 12/510,651, filed Jul. 28, 2009 (Inventor—Gibbins).
Amendment Entered with CPA/RCE filed on Feb. 19, 2010 for U.S. Appl. No. 11/194,951, filed Aug. 1, 2005 (Inventor—Karandikar et al.).
Notice of Appeal filed on Oct. 21, 2009 for U.S. Appl. No. 11/194,951, filed Aug. 1, 2005 (Inventor—Karandikar et al.).
Final Rejection issued on May 21, 2009 for U.S. Appl. No. 11/194,951, filed Aug. 1, 2005 (Inventor—Karandikar et al.).
Response After Non-Final Rejection filed on Feb. 5, 2009 for U.S. Appl. No. 11/194,951, filed Aug. 1, 2005 (Inventor—Karandikar et al.).
Non-Final Rejection issued on Aug. 5, 2008 for U.S. Appl. No. 11/194,951, filed Aug. 1, 2005 (Inventor—Karandikar et al.).
Response to Election / Restriction filed on Feb. 5, 2008 for U.S. Appl. No. 11/194,951, filed Aug. 1, 2005 (Inventor—Karandikar et al.).
Requirement for Restriction/Election issued on Dec. 5, 2007 for U.S. Appl. No. 11/194,951, filed Aug. 1, 2005 (Inventor—Karandikar et al.).

* cited by examiner

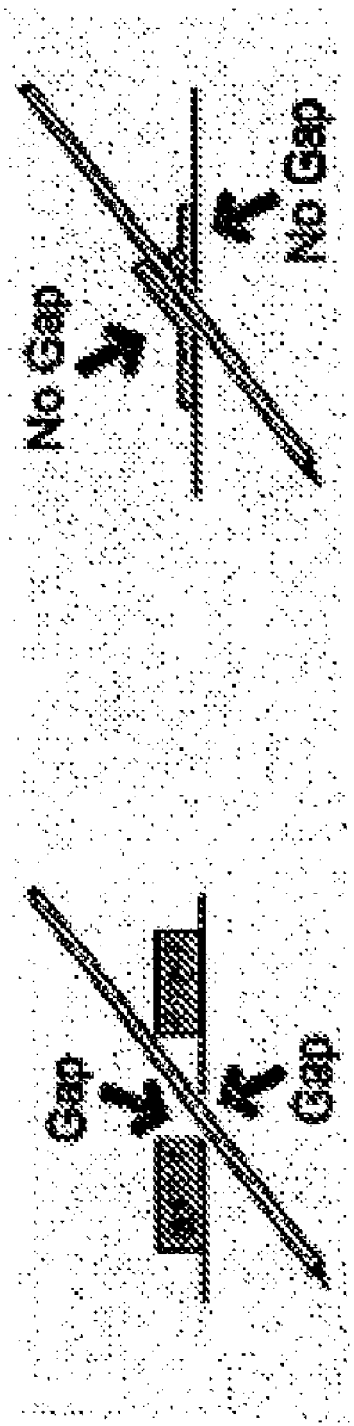

US 8,293,965 B2

ANTIMICROBIAL SITE DRESSINGS

RELATED APPLICATIONS

This application claims the priority of U.S. Provisional Patent Application No. 60/796,039, filed Apr. 28, 2006, which is herein incorporated in its entirety.

FIELD OF THE INVENTION

The present invention relates to antimicrobial articles for the protection of percutaneous device access sites and methods of use the same.

BACKGROUND OF THE INVENTION

According to the United States Centers for Disease Control and Prevention (CDC), an estimated 250,000 cases of bloodstream infections associated with central venous catheters occur each year in U.S. hospitals. These infections add approximately $25,000 in patient care costs per episode. In addition, the mortality associated with these infections is 18% or 45,000 deaths per years in the United States, see, CDC, Guidelines for the Prevention of Intravascular Catheter-Related Infections, Recommendations and Reports, Morbidity and Mortality Weekly Report, Aug. 9, 2002, Vol. 51, No. RR-10.

Various antimicrobial dressings have been used to prevent and/or reduce infections related to the uses of percutaneous devices. For example, BioPatch® Dressing from Johnson and Johnson is reported to reduce the incidence of catheter-related bloodstream infection by 60% and local infection by 44%. This polyurethane foam with chlorhexidine gluconate (CHG) may be used together with vascular percutaneous devices such as central venous catheters, arterial catheters, and PICC lines, as well as non-vascular percutaneous devices, such as orthopedic pins, epidural catheters, and drain tubes. It may continuously deliver the antimicrobial CHG for up to seven days and absorb up to eight times its weight in fluid. In addition, Acticoat 7 (with SILCRYST™ Nanocrystals) Antimicrobial Barrier Dressing provides an effective barrier to bacterial penetration, which may help reduce infection in partial and full thickness wounds. It contains a nanocrystalline coating of pure silver for delivering antimicrobial barrier activity to a dermal site, a rayon/polyester core for managing moisture level and controlling silver release, and a silver-coated high-density polyethylene mesh for facilitating the passage of silver through the dressing. It is reported that in vitro tests indicated that the Acticoat 7 dressing may be effective against more than 150 pathogens, such as, resistant strains of bacteria (e.g., antibiotic-resistant strains of *Pseudomonas*, methicillin-resistant *Staphylococcus aureus* (MRSA), vancomycin-resistant *Enterococcus* (VRE)) and fungi.

Nonetheless, a number of factors limited the applications and/or the efficacies of the existing products. For example, it is well known that CHG can cause hypersensitivity reactions and has not been proven safe for pediatric applications. In addition, too much silver ions released from a dressing may cause dermal discoloration and may also be cytotoxic. Another drawback of the dressings currently known in the art is that these dressings have only point or two-dimensional contacts with a percutaneous device, leaving gaps between the dressing and the device and exposing the percutaneous device access site to potential pathogen attacks.

Therefore, there exists a need for an antimicrobial article for use with a percutaneous device having features, such as, providing a minimized or reduced gap between the article and the percutaneous device for reducing, minimizing, or eliminating infections related to the use of such percutaneous device, providing a sustained release of antimicrobial agents, facilitating the maintenance of optimal moisture balance, and/or being non- or less toxic, non- or less irritating, non- or less staining, and/or non- or less sensitizing.

SUMMARY OF THE INVENTION

The present invention provides an article of manufacture for use with a percutaneous device, comprising a matrix, wherein the matrix comprises a first passage, a second passage, and an antimicrobial agent, wherein the first passage connects to the second passage, and wherein the matrix contacts a percutaneous device in a three-dimensional mode. In one embodiment, a first passage may extend from an edge of the matrix toward an internal point of the article. In another embodiment, a second passage may connect with the first passage at one end of the first passage. In yet another embodiment, at least a portion of a second passage comprises a curved shape. In still another embodiment, the antimicrobial agent may be a silver-containing antimicrobial agent, such as, without limitation, a silver compound or a metallic silver (e.g., a silver anoparticle). The silver containing antimicrobial agent may be released when the antimicrobial article is applied. In addition, the antimicrobial article of the present invention may donate moisture to a dry dermal site (e.g., a dry wound bed) and/or absorb liquid or exudates of a dermal site.

The present invention also provides a method of treating or preventing an infection comprising contacting a percutaneous device and the percutaneous device access site with the antimicrobial article of the present invention.

Other features and advantages of the present invention will become apparent from the following detailed description. It should be understood, however, that the detailed description and the specific examples, while indicating the preferred embodiments of the present invention, are given by way of illustration only, since various changes and modifications within the spirit and scope of the present invention will become apparent to those skilled in the art from this detailed description.

BRIEF DESCRIPTION OF FIGURES

FIG. 2 shows a representative schematic diagram of an interaction between a percutaneous device and a dressing known in the art.

FIG. 3 shows a representative schematic diagram of an interaction between a percutaneous device and an antimicrobial article produced in accordance with one embodiment of the present invention.

DETAILED DESCRIPTION OF THE INVENTION

Figure 1:
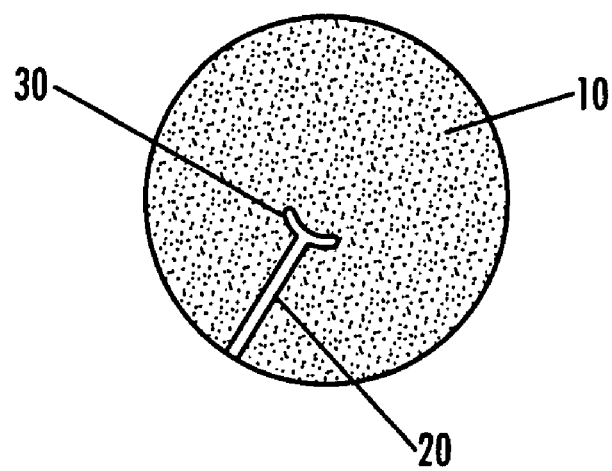
FIG. 1 shows a representative antimicrobial article produced in accordance with one embodiment of the present invention.

As used herein and in the appended claims, the singular forms "a," "an," and "the" include plural references, unless the content clearly dictates otherwise. Thus, for example, reference to "an antimicrobial agent" includes a plurality of such antimicrobial agents and equivalents thereof known to those skilled in the art, and reference to "the matrix" is a reference to one or more such matrices and equivalents thereof known to those skilled in the art, and so forth. All publications, patent applications, patents, and other references mentioned herein are incorporated by reference in their entirety.

The present invention generally relates to novel articles and methods for controlling bioburden and managing moisture level at, around, or adjacent to a percutaneous device assess site. The article of the present invention may have at least one of the features, such as, providing a minimized or reduced gap between the article and the percutaneous device for reducing, minimizing, or eliminating infections related to the use of such percutaneous device, providing a sustained release of antimicrobial agents, facilitating the maintenance of optimal moisture balance, and/or being non- or less toxic, non- or less irritating, non- or less staining, and/or non- or less sensitizing. For example, the present invention provides articles which may provide broad spectrum antimicrobial agents to a percutaneous device assess site which may prevent MSRA and VRE infection for up to seven days. It may also provide moisture to a dry percutaneous device assess site and/or absorb more than about five times its weight in exudates from the percutaneous device access site.

The term "percutaneous device," as used herein, includes any devices which administer, remove, absorb, and/or release a substance, or access and/or monitor, by way of, or effect through, the skin. For example, a percutaneous device may be a medical device which accesses inner organs or other tissue via needle-puncture or other methods of transit of the skin. It may also be a medical device which effect through an "opened" skin, where, for instance, the skin was opened using a medical device, such as, a scalpel, followed by the administration of the percutaneous device and then the closing of the opening. Examples of percutaneous devices include, without limitation, a vascular device (such as, an intravenous catheter, a central venous line, an arterial catheter, a peripheral catheter, or a dialysis catheter), or a non-vascular device (such as, an external fixator pin, a peritoneal dialysis catheter, an epidural catheter, a chest tube, or a gastronomy feeding tube).

In one aspect, the present invention provides an article of manufacture for use with a percutaneous device, comprising a matrix, wherein the matrix comprises a first passage, a second passage, and an antimicrobial agent, wherein the first passage connects to the second passage, and wherein the matrix may contact a percutaneous device in a three-dimensional mode. FIG. 1 illustrates a representative example of the article produced in accordance with one embodiment of the present invention, which comprises a matrix 10, a first passage [the slit 20], a second passage [the slit 30], and silver-based antimicrobial agents.

The matrix may be in any shape suitable for the purposes of the application and may be fabricated using any suitable materials known in the art. In one embodiment, the matrix may be in the shape of a disc. In another embodiment, the matrix may contain a biocompatible material. For example, the matrix may contain a plurality of layers and at least the layer which has access to a dermal site may be made using a biocompatible material. In yet another embodiment, the matrix may contain a swellable material which may confer certain desirable features to the article of the present invention, such as, to allow it to absorb wound exudates. Examples of materials for producing the matrix of the present invention may include, without limitation, those taught in U.S. Pat. Nos. 7,160,553; 6,897,349; 6,605,751; 6,355,858; 5,928,174; 5,833,665; and 5,196,190, and U.S. Patent Application Publication Nos. 2007/0003603; 2005/0226931, 2001/0041188; and U.S. patent application Ser. Nos. 11/572,899; 11/663,236; and 11/704,167. All of which are hereby incorporated in their entirety.

An aspect of the present invention, the active agent, which may be a heavy metal ion, such as silver, is incorporated into the matrices so that the agent is released directly from the matrices and delivered to the contact substrate such as the dermal site or the percutaneous device. The incorporated active agents may be released over a period of time, and in this way, the articles of the present invention retain their ability to kill or inhibit microorganisms over an extended period of time. As used herein, the term silver includes all silver salts or silver compounds, including, but not limited to, silver chloride, silver phosphate, silver sulfate, silver iodide or silver bromide. The active form of the silver salt is the silver ion, as is the case for the active forms of the heavy metals.

In one embodiment, the matrix of the present invention may comprise a hydrophilic matrix material, which may be flexible and elastic, and may be permeable to substances such as inorganic salts, aqueous fluids, and dissolved gaseous agents including oxygen. The hydrophilic matrix material may be a natural, synthetic, or semi-synthetic polymer. Examples of the polymers that may be used for the construction of the antimicrobial article include, but are not limited to, collagen, animal hide, hyaluronic acid, dextran, alginate, hydrophilic fibers of cross-linked and/or non-cross-linked celluloses (such as carboxymethy cellulose and hydroxymethyl cellulose), cotton, rayon, fibers made from polyacrylates, fibers of calcium alginates, polyacrylamide, polyvinyl's (PVP, and PVC), polyacrylate, polybuterate, polyurethane foam, silicone elastomer, rubber, nylon, vinyl, and cross linked dextran. For instance, the matrix of the present invention may comprise polymerized chains of acrylamide monomer, wherein the acrylamide monomers may be cross-linked with a cross-linking agent (e.g., methylenebisacrylamide, bisacrylylycystamine, or diallyltartar diamide). In embodiments where cross-linked dextran is used, the molecular weight of the dextran polymer may be between about 50,000 and about 500,000. Methods for making matrices using these polymers (e.g. polyacrylamide polymer) are well known in the art.

The matrix of the present invention may be moist or dry, which may facilitate the management of moisture balance at or near a percutaneous device access site. In one embodiment, the matrix may comprise water, such as, about 10-40% of water or about 20% water, which may provide moisture to a dry dermal site. In another embodiment, the matrix may absorb liquid, such as, exudates from a percutaneous device access site. For example, the matrix may absorb up to about five times its weight in liquid, such as, exudates from a percutaneous device access site.

In addition, the matrix of the present invention may be translucent, semi-transparent, or transparent, which may allow for visualization and monitoring the percutaneous device access site.

An example of a matrix of the present invention comprises a natural or synthetic polymer and a non-gellable polysaccharide. Natural hydrophilic polymers that may be used include, but are not limited to collagen, animal hide, hyaluronic acid, dextran and alginate. Additionally included are hydrophilic fibers of cross-linked and non-cross-linked celluloses such as carboxymethyl cellulose and hydroxymethyl cellulose; cotton, rayon, and of fibers made from polyacrylates; and fibers of calcium alginates that may be used. Synthetic polymers that may be used include, but are not limited to polyacrylamide, polyvinyl's (PVP, and PVC), polyacrylate, polybuterate, polyurethane foam, silicone elastomer, rubber, nylon, vinyl or cross linked dextran. If cross-linked dextran is used, it is preferred that the molecular weight of the dextran polymer is between 50,000 and 500,000. Non-gellable polysaccharide may include a non-gellable galactomannan macromolecule such a guar gum. A range of guar gum between approximately 0.01 kg to 100 kg, between approximately 0.1 kg to 10 kg, or between approximately 0.5 kg to 2 kg is generally sufficient. Other non-gellable polysaccharides may include lucerne, fenugreek, honey locust bean gum, white clover bean gum and carob locust bean gum.

Should it be desired to decrease the permeability of the articles of the present invention, water loss control agents may be applied to one or more surfaces of the device. Water loss control agents are known in the art and include, but are not limited to, petrolatum, glycolipids, ceramides, free fatty acids, cholesterol, triglycerides, sterylesters, cholesteryl sulfate, linoleic ethyl ester and silicone oil.

If desired, a plasticizer may also be added to the matrix material. Plasticizers are known in the art. An example of a plasticizer is glycerol and water, however, propylene glycol and butanol may also be used. If glycerol is used, a range of between approximately 0.5 kg to 50 kg, between 1 kg and 30 kg, or between approximately 5 kg to 15 kg is generally sufficient. The plasticizer may be added in the initial mixture of polymer and cross-linking agent.

If desired, a hydration control agent may be incorporated into the matrix. A hydration control agent that may be used is an isopropyl alcohol, however, ethanol, glycerol, butanol, and propylene glycol may also be used. A range of isopropyl alcohol of between approximately 0.1 kg to 10 kg, between approximately 0.2 kg to 5 kg and between approximately 0.5 kg to 2 kg is generally sufficient.

An embodiment of a matrix of the present invention may comprise polymerized chains of acrylamide monomer, wherein the acrylamide monomers are cross-linked with a cross-linking agent, a non-gellable polysaccharide, and an active agent or pharmaceutical directly incorporated into the matrix. The active agent, such as a silver-containing compound, may be added during the formation of the matrix or after matrix formation. A range of acrylamide between approximately 1 kg to 100 kg, between approximately 2 to 50 kg, or between approximately 5 kg to 20 kg is generally sufficient. An example of a matrix comprising cross-linked polyacrylamide and guar gum is disclosed in U.S. Pat. No. 5,196,160 to Nangia.

A cross-linking agent is NNNN'-methylenebisacrylamide, and other appropriate cross-linking agents such as bisacrylylycystamine and diallyltartar diamide may also be used. If NNNN'-methylenebisacrylamide is used, a range of between approximately 0.01 kg to 1 kg, between approximately 0.02 kg to 0.5 kg, or between approximately 0.05 kg to 0.3 kg is generally sufficient. As noted above, non-gellable polysaccharide include a non-gellable galactomannan macromolecule such a guar gum, but other non-gellable polysaccharides may include lucerne, fenugreek, honey locust bean gum, white clover bean gum and carob locust bean gum.

Ammonium persulfate and TEMED (N,N,N'N'-tetramethylethylene diamine) may also be added to the matrix. A range of ammonium persulfate between approximately 0.01 kg to 1 kg, between approximately 0.02 kg to 0.5 kg, or between approximately 0.05 kg to 0.2 kg is generally sufficient. Additionally, a range of TEMED between approximately 0.01 kg to 1 kg, between approximately 0.02 kg and 0.5 kg, or between approximately 0.05 kg to 0.3 kg is generally sufficient.

The matrix of the present invention may further comprise various additives as well as other active or inactive agents and/or components, such as, without limitation, a water loss control agent (e.g., petrolatum, glycolipids, ceramides, free fatty acids, cholesterol, triglycerides, sterylesters, cholesteryl sulfate, linoleic ethyl ester, or silicone oil), a plasticizer (e.g., glycerol, propylene glycol, and butanol), a hydration control agent (e.g., isopropyl alcohol, ethanol, glycerol, butanol, and propylene glycol). In one embodiment, the matrix of the present invention may comprise a non-gellable polysaccharide, such as, without limitation, a non-gellable galactomannan macromolecule (e.g., a guar gum), lucerne, fenugreek, honey locust bean gum, white clover bean gum, and carob locust bean gum. The term "active agent" as used herein may include, without limitation, antimicrobial agents, gases, mycoplasma treatments, growth factors, proteins, nucleic acids, angiogenic factors, anesthetics, mucopolysaccharides, metals, pharmaceuticals, chemotherapeutic agents, herbicides, growth inhibitors, growth promoters, wound healing agents, indicators of change in the environment, enzymes, nutrients, vitamins, minerals, carbohydrates, fats, fatty acids, nucleosides, nucleotides, amino acids, sera, antibodies and fragments thereof, lectins, immune stimulants, immune suppressors, coagulation factors, neurochemicals, cellular receptors, antigens, adjuvants, radioactive materials, and combinations thereof. In one embodiment, the matrix of the present invention may comprise a plurality of growth factor agents, which include, without limitation, basic fibroblast growth factor (bFGF), acidic fibroblast growth factor (aFGF), nerve growth factor (NGF), epidermal growth factor (EGF), insulin-like growth factors 1 and 2, (IGF-1 and IGF-2), platelet derived growth factor (PDGF), tumor angiogenesis factor (TAF), vascular endothelial growth factor (VEGF), corticotropin releasing factor (CRF), transforming growth factors α and β (TGF-α and TGF-β), granulocyte-macrophage colony stimulating factor (GM-CSF), the interleukins (e.g., interleukin-8), and the interferons.

In another embodiment, the matrix of the present invention may comprise proteins that may be useful in the treatment of wounds include, without limitation, collagen, cross-linked collagen, fibronectin, laminin, elastin, and cross-linked elastin, or combinations and fragments thereof. In yet another embodiment, the matrix of the present invention may comprise acid mucopolysaccharides including, without limitation, heparin, heparin sulfate, heparinoids, dermatan sulfate, pentosan polysulfate, chondroitin sulfate, hyaluronic acid, cellulose, agarose, chitin, dextran, carrageenin, linoleic acid, and allantoin. In addition, adjuvants or compositions that boost an immune response, as well as antibodies or antibody fragments, may also be used in conjunction with the antimicrobial article of the present invention.

The article of the present invention may contain a plurality of passages, or slits. The passages of the present invention may be in any suitable shape or form, such as, without limitation, a linear form, a curved formed, an irregular form, or combinations thereof. In one embodiment, the first passage may be a slit which may extend from an edge of the matrix, for example, as illustrated in FIG. 1 (Slit 20). In another embodiment, the second passage may comprise a curved shape. The second passage may connect with the first passage at any suitable point/location on the second passage. For example, the first slit 20 may connect with the second slit 30 at the middle of the second slit 30, as illustrated in FIG. 1.

Unlike the devices known in the art, the article of the present invention may contact a percutaneous device in a three-dimensional mode, for example, without limitation, as illustrated in FIG. 3. Conventional dressings associate with a percutaneous device through a point contact or through a two-dimensional contact, i.e., all the contacts between the dressings and the percutaneous device are planar contacts which occur on the same plane, see, e.g., FIG. 2. The association of a conventional dressing and a percutaneous device in such modes leaves considerable gaps between the conventional dressing and the percutaneous device, as well as leaves the percutaneous device and the percutaneous device access site available for exposure to various pathogens. In comparison, the three-dimensional interaction between the article of the present invention and a percutaneous device substantially reduces, minimizes, or eliminates the gap between these devices while simultaneously reducing, minimizing, or eliminating the exposure of the percutaneous device access site to various pathogens, see, e.g., FIG. 3.

The article of the present invention may contain at least one antimicrobial agent. The term "antimicrobial agent" as used herein includes a substance, such as a compound or an ion, that is capable of destroying or inhibiting the growth and/or proliferation of a microorganism, such as, an anti-bacterial agent, an anti-fungal agent, an anti-viral agent, and/or an anti-parasitic agent. An antimicrobial agent may be a composition produced by or derived from certain bacteria, fungi, plants, and other organisms, and derivatives and variants thereof. An antimicrobial agent may also be synthesized or semi-synthesized chemically. In one embodiment, an antimicrobial agent may be a salt, a small molecule organic compound, a lipid, a carbohydrate, a polypeptide, a nucleic acid, or combinations thereof. Examples of antimicrobial agents include, without limitation, acyclovir, amphotericin B, ampicillin, atovaquone, azithromycin, bacitracin, carbomycin, cephalosporin, chloramphenicol, chlorotetracyclin, ciprofloxacin, clarithromycin, clindamycin, clofazimine, cycloheximide, dapsone, diclazaril, doxycycline, erythromycin, ethambutol, fluconazole, fluoroquinolones, foscamet, fumigillin, ganciclovir, gentamicin, griseofulvin, iatroconazole, kanamycin, ketoconazole, lincomycin, methicillin, miconazole, neomycin, ofloxacin, oleandomycin, paromomycin, penicillin, pentamidine, polymyxin-B, pyrazinamide, pyrimethamine, rifabutin, rifampicin, rifamycin, sparfloxacin, streptomycin, sulfadiazine, tetracycline, trifluorouridine, vancomycin, and Zn-pyrithione, as well as heavy metals including, without limitation, copper, gold, platinum, silver, and zinc, and combinations thereof including, e.g., salts, such as chloride, bromide, iodide, and periodate, and complexes with carriers, and other forms.

In one embodiment, the antimicrobial agent may be a silver-containing antimicrobial agent, such as, without limitation, a silver-containing compound or complex, or a silver nanoparticle. Various silver-containing antimicrobial agents suitable for the purposes of the present invention are known in the art, such as, those disclosed in U.S. Pat. Nos. 7,160,553; 6,897,349; 6,605,751; 6,355,858; 5,928,174; 5,833,665; and 5,196,190, and U.S. Patent Application Publication Nos. 2007/0003603; 2005/0226931, 2001/0041188; and U.S. patent application Ser. Nos. 11/572,899; 11/663,236; and 11/704,167. All of which are incorporated in their entireties.

The release of an antimicrobial agent, e.g., a silver-based antimicrobial agent, may be a sustained or controlled release. Methods for formulating a sustained/controlled release composition for medical applications are well known in the art. For example, the article of the present invention may comprise a water-containing, polyacrylate hydrophilic matrix and silver nanoparticles as the antimicrobial agents. Such a matrix has been shown to be capable of releasing silver ions in a sustained mode over an extended period of time, such as, up to seven days. In various embodiments of the present invention, the release of silver ions to a percutaneous device access site may be influenced by the release of exudates from the percutaneous device access site, wherein the exposure to wound moisture dissolves the silver reservoir and stimulates the release of silver ions into the wound site. The sustained release of silver means fewer dressing changes, which may result in less exposure of the percutaneous access site to the environment, and thus, reduce the risk of infection and lower hospital costs.

In another aspect, the present invention provides a method of treating or preventing an infection, comprising contacting a percutaneous device and a percutaneous device access site with the antimicrobial article of the present invention. The infection may be any infection caused by a microbial pathogen, such as, a bacterium, a fungus, a virus, and/or a parasite.

Whereas this invention has been described in detail with particular reference to preferred embodiments, it is understood that variations and modifications can be effected within the spirit and scope of the invention, as described herein before and as defined in the appended claims. The corresponding structures, materials, acts, and equivalents of all means plus function elements, if any, in the claims below are intended to include any structure, material, or acts for performing the functions in combination with other claimed elements as specifically claimed.

EXAMPLE 1

Light Stable Silver Salt Matrix

It has been found that silver salts such as silver chloride are generally stable in the salt form. Moreover, many silver salts such as silver phosphate and silver sulfate are only weakly soluble in aqueous solvent. Methods of the present invention comprise preparing a salt of silver during the preparation of the matrix, and preferably the matrix is a hydratable polyacrylate polymer.

The formation of the weakly soluble salt, silver chloride, is fully dispersed throughout the matrix and provide the precursor for the formation of the sustained release silver. The deposition of collodial silver chloride or other weakly soluble salt throughout the matrix is accomplished by any one of several methods of the present invention. In one method, the pre-formed salt, such as silver chloride, was incorporated along with other components during the compounding of the matrix formulation prior to polymerization. Another method comprises sequentially adsorbing or absorbing solutions comprising the precursor components, such as weakly soluble salts into a matrix. For example, a solution containing chloride ions was added to a polymerized hydrophilic matrix, where the solution was adsorbed or absorbed by the matrix. A second solution, containing silver ions, was added to the matrix to form a colloid of silver chloride in the matrix. Another method, is the sequential addition of anions and cations, in no particular order, during the compounding of the material mixture, causing the formation and dispersion of the colloid in the mixture prior to polymerization.

Chloride ions comprise any dissociable salt, including, but not limited to, sodium chloride, potassium chloride, copper chloride, ferric chloride, zinc chloride calcium chloride and hydrochloric acid. Such chloride ions may be added in solution or dry form.

An ionic silver solution comprises compositions such as those prepared by dissolving a salt of silver, including but not limited to silver nitrate, silver acetate, silver citrate, and silver sulphate, into water. The silver ions may also be added in a dry form.

When the polymer was catalyzed to gel, the finely dispersed silver chloride was immobilized within the polymer.

Since AgCl is only weakly soluble in aqueous solutions the re-association to AgCl is strongly favored. However the ionic form is unstable and may react to light to form insoluble elemental silver ($Ag_o$). This form has minimal antimicrobial activity and moreover is a black precipitate that strongly discolors the matrix when it is formed. In addition the ionic form ($Ag^+$) is highly reactive with functional electron donating groups which may reduce its antimicrobial effect. Therefore it is desirable to stabilize the silver by providing an excess of chloride ions in the matrix.

A matrix comprising a polyacrylate hydratable matrix produced according to U.S. Pat. No. 5,196,190 and containing silver was made using the following steps. The silver containing polyacrylate matrix was made by mixing 185 g acrylamide and 2 g bisacrylamide into 3330 g of water containing between 33.3 g of sodium chloride. To this mixture, was added 21 g of guar gum and 188 g of glycerol. After mixing to homogeneity, a solution containing 0.563 g silver nitrate was slowly added to the mixing batch. The polymerization of the mixture was accomplished by blending 1.8 ml TEMED and 2.6 g ammonium persulphate into the mixture. The mixture was poured into the appropriate molds before polymerization in a dark place. The gelled polymer was removed from the mold, dehydrated by mild heat in a darkened drier and then rehydrated by humidification to a desired moisture content, 22% w/w. The matrix was then cut to form the article with one or two passages for use with percutaneous devices.

EXAMPLE 2

The present invention also comprises compositions and devices comprising preformed hydrophillic fiber matrices and methods for making and using such materials with antimicrobial activity. Pre-formed cross-linked hydrophilic fibers are readily available through commercial channels for on-processing, packaging and sterilization for use in wound and other medical applications. Incorporation of silver into fibrous materials by an impregnation method that causes the in situ formation of a stabilized silver colloid complex within and around the fibrous material was used to make matrices for the present invention.

One method of making materials with antimicrobial activity was to disperse a chloride salt of sodium or copper or iron in water at a concentration that remains in solution when the water was combined with an alcohol solvent, including, but not limited to, isopropyl alcohol and ethanol. The fibrous matrix materials for impregnation were then immersed in a bath of the chloride ions so that the material is completely immersed. After a suitable time the material was then removed and blotted of excess chloride-containing solvent. Then the material was immersed in a similar aqueous/alcohol bath that contains silver and copper or iron ions. After a suitable time, the material is removed, blotted of excess reagent and air dried. It is desirable that the ratio of water to alcohol in mixtures that contain the ionic elements not exceed a concentration that would cause hydrophilic materials to begin to gel. A range comprises 5-15% aqueous, and it is suggested that the aqueous portion not be greater than 50%. Reversal of the immersion sequence is inconsequential to the success of impregnation of the fibrous materials.

Hydrophilic fibrous polymer materials such as cross-linked carboxymethyl cellulose, calcium alginates and textiles such as cotton comprising silver-containing compounds provide matrices for the present invention. These hydrophilic materials aggressively absorb aqueous solutions which often cause gelling of the matrix materials. Gelled materials may be subsequently dehydrated, but seldom retain their original properties after absorption of water. Therefore it is impractical to use a substantially aqueous vehicle for the delivery of ionic silver and chloride into the matrix material where nucleation in situ of colloid would be expected to occur. This excludes the method of precipitating AgCl in situ using water as solvent. These hydrophilic polymers do not absorb alcohol, therefore a AgCl precipitation in a water:alcohol solution to partially hydrate fibers with reagents was performed.

A. This experiment showed the use of either acetone, isopropyl alcohol or ethanol as the solvent phase of an aqueous:alcohol bath for impregnation of silver into cross-linked carboxymethyl cellulose.

The following combinations of reagents were produced and tested for efficacy in allowing nucleation of AgCl in the solvent phase. 1) Add 0.177 g NaCl to 3.333 mL $H_2O$. 2) Add 90 g Acetone, IPA, or EtOH. Add 6.666 mL $AgNO_3$ sol (0.11325 g/50 ml $H_2O$) It was concluded that the ethanol was the preferred alcohol for the delivery vehicle.

The nucleation of silver chloride colloid in the hydrophilic polymer was accomplished by preparing an aqueous:alcohol solution of sodium chloride in which various hydrophilic materials were immersed. After an appropriate time an aqueous:alcohol solution containing silver nitrate was added. The materials were then removed, blotted of excess materials and air dried. They were then tested for antimicrobial activity against Staph. aureus by zone inhibition assay, for skin staining properties and for discoloration in light. 1) Added 0.1777 g NaCl to 2 ml $H_2O$ 2) Added 0.006795 g $AgNO_3$ to 100 µl $H_2O$ 3) Added 25 g EtOH to NaCl and $AgNO_3$ solutions 4) Place a 2×2 inch square of Tegagen, Algisite M, Aquacel, or Algisite Rope into the NaCl solutions. 5) After a few seconds, add the $AgNO_3$ solution. 6) After a few seconds, remove dressings and blot dry. 7) Test for sustained release on staph zone inhibition plates, for skin staining, expose to light.

Silver was incorporated into hydrophilic fibers in amounts that allowed for sustained release. IPA or acetone may be used with more soluble chloride salts ($CuCl_2$, $FeCl_3$) but ethanol was used with sodium chloride. The resulting materials possessed antimicrobial activity and do not appreciably discolor in the presence of light.

What is claimed is:

1. An article of manufacture for use with a percutaneous device, comprising, a matrix, wherein a first portion of the matrix is formed as a generally planar member, and wherein the matrix defines a passage and a curve-shaped slit having a first end, a second end, and a middle, wherein the passage extends from an edge of the matrix to a portion of the curve-shaped slit between the first and second ends of the curve-shaped slit, wherein the matrix further comprises: an antimicrobial agent; and a second portion of the matrix, defined by the intersection of the passage and the curve-shaped slit, wherein the second portion of the matrix forms a three-dimensional contact with the percutaneous device above the surface of the skin, wherein the first portion of the matrix and the second portion of the matrix are in different planes from each other above the surface of the skin.

2. The article of claim 1, wherein the antimicrobial agent is a silver containing compound.

3. The article of claim 1, wherein the matrix further comprises at least one additional active agent.

4. The article of claim 3, wherein the active agent is an antifungal agent, an antibacterial agent, an anti-viral agent, an antiparasitic agent, an anaesthetic, a mucopolysaccharide, a growth factor, a protein, an angiogenic factor, a wound healing agent or adjuvant, or combinations thereof.

5. The article of claim 4, wherein the protein is collagen, cross-linked collagen, fibronectin, laminin, elastin, cross-linked elastin, antibodies, or combinations or fragments thereof.

6. The article of claim 4, wherein the growth factor is basic fibroblast growth factor, acidic fibroblast growth factor, nerve growth factor, epidermal growth factor, insulin-like growth factors 1 and 2, platelet derived growth factor, tumor angiogenesis factor, vascular endothelial growth factor, corticotrophin releasing factor, transforming growth factors, alpha. and .beta., interleukin-8, granulocyte-macrophage colony stimulating factor, interleukins, or interferons.

7. The article of claim 4, wherein the mucopolysaccharide is heparin, heparin sulfate, heparinoids, dermatan sulfate, pentosan polysulfate, chondroitin sulfate, hyaluronic acid, cellulose, agarose, chitin, dextran, carrageenin, linoieic acid, or allantoin.

8. The article of claim 1, wherein the antimicrobial agent is isoniazid, ethambutol, pyrazinamide, streptomycin, clofazimine, rifabutin, fluoroquinolones, ofloxacin, sparfloxacin, rifampin, azithromycin, clarithromycin, dapsone, tretracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycine, diclazaril, acyclovir, trifluorouridine, foscarnet, penicillin, gentamicin, ganciclovir, iatroconazole, Zn-pyrithione, silver salts of chloride, bromide, iodide or periodate.

9. The article of claim 1, wherein the matrix is made from a natural or synthetic hydrophilic polymer.

10. The article of claim 9, wherein the polymer is collagen, animal hide, hyaluronic acid, dextran, alginate, hydrophilic fibers of cross-linked and/or non-cross-linked celluloses, carboxymethy cellulose, hydroxymethyl cellulose, cotton, rayon, fibers made from polyacrylates, fibers of calcium alginates, polyacrylamide, polyvinyls, PVP, PVC, polyacrylate, polybuterate, polyurethane foam, silicone elastomer, rubber, nylon, vinyl, or cross linked dextran.

11. The article of claim 1, wherein the passage extends from the edge of the matrix to the middle of the slit.

12. The article of claim 1, wherein the curve-shaped slit is defined by two ends that are not connected together.

13. The article of claim 1, wherein the matrix is translucent, semi-transparent, or transparent.

14. A method of treating or preventing an infection, comprising, contacting a percutaneous device with a matrix, wherein a first portion of the matrix is formed as a generally planar member, wherein the matrix defines a passage and a curve-shaped slit having a first end, a second end, and a middle, wherein the passage extends from an edge of the matrix to a portion of the curve-shaped slit between the first and second ends of the curve-shaped slit, wherein the matrix further comprises: an antimicrobial agent, wherein contacting the percutaneous device comprises selectively forming a three-dimensional contact with a portion of the percutaneous device, in which a second portion of the matrix, defined by the intersection of the passage and the curve-shaped, forms contact with the percutaneous device above the surface of the skin, wherein the first portion of the matrix and the second portion of the matrix are in different planes from each other above the surface of the skin.

15. The method of claim 14, wherein the antimicrobial agent is a silver containing compound.

16. The method of claim 14, wherein the matrix further comprising comprises at least one additional active agent in the matrix.

17. The method of claim 16, wherein the active agent is an antifungal agent, an antibacterial agent, an anti-viral agent, an antiparasitic agent, an anaesthetic, a mucopolysaccharide, a growth factor, a protein, an angiogenic factor, a wound healing agent or adjuvant, or combinations thereof.

18. The method of claim 17, wherein the protein is collagen, cross-linked collagen, fibronectin, laminin, elastin, cross-linked elastin, antibodies, or combinations or fragments thereof.

19. The method of claim 17, wherein the growth factor is basic fibroblast growth factor, acidic fibroblast growth factor, nerve growth factor, epidermal growth factor, insulin-like growth factors 1 and 2, platelet derived growth factor, tumor angiogenesis factor, vascular endothelial growth factor, corticotrophin releasing factor, transforming growth factors alph. and .beta., interleukin-8, granulocyte-colony stimulating factor, interleukins, or interferons.

20. The method of claim 17, wherein the mucopolysaccharide is heparin, heparin sulfate, heparinoids, dermatan sulfate, pentosan polysulfate, chondroitin sulfate, hyaluronic acid, cellulose, agarose, chitin, dextran, carrageenin, linoleic acid, or allantoin.

21. The method of claim 14, wherein the antimicrobial agent is isoniazid, ethambutol, Pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclarzaril, acyclovir, trifluorouridine, foscarnet, penicillin, gentamicin, ganciclovir, iatroconazole, microazole, Zn-pyrithione, silver salts of chloride, bromide, iodide or periodate.

22. The method of claim 14, wherein the matrix is made from a natural or synthetic hydrophilic polymer.

23. The method of claim 22, wherein the polymer is collagen, animal hide, hyaluronic acid, dextran, alginate, hydrophilic fibers of cross-linked and/or non-crosslinked celluloses, carboxymethy cellulose, hydroxymethyl cellulose, cotton, rayon, fibers made from polyacrylates, fibers of calcium alginates, polyacrylamide, polyvinyls, PVP, PVC, polyacrylate, polybuterate, polyurethane foam, silicone elastomer, rubber, nylon, vinyl, or cross linked dextran.

24. The method of claim 14, wherein the passage extends from the edge of the matrix to the middle of the slit.

25. The method of claim 14, wherein the curve-shaped slit is defined by two ends that are not connected together.

26. The method of claim 14, wherein the matrix is translucent, semi-transparent, or transparent.

* * * * *